(12) United States Patent
Hamdouchi et al.

(10) Patent No.: US 8,383,642 B2
(45) Date of Patent: Feb. 26, 2013

(54) SPIROPIPERIDINE COMPOUNDS

(75) Inventors: Chafiq Hamdouchi, Carmel, IN (US); Jayana Pankaj Lineswala, Brownsburg, IN (US); Pranab Maiti, Bangalore (IN)

(73) Assignee: Eli Lilly and Company, Indidnapolis, IN (US)

( * ) Notice: Subject to any disclaimer, the term of this patent is extended or adjusted under 35 U.S.C. 154(b) by 162 days.

(21) Appl. No.: 12/901,597

(22) Filed: Oct. 11, 2010

(65) Prior Publication Data

US 2011/0092531 A1 Apr. 21, 2011

Related U.S. Application Data

(60) Provisional application No. 61/251,839, filed on Oct. 15, 2009, provisional application No. 61/303,334, filed on Feb. 11, 2010.

(51) Int. Cl.
  *C07D 401/04* (2006.01)
  *A61K 31/438* (2006.01)
(52) U.S. Cl. ............... 514/278; 546/17; 546/18
(58) Field of Classification Search .......... 546/17, 546/18; 514/278
See application file for complete search history.

(56) References Cited

U.S. PATENT DOCUMENTS

| | | | |
|---|---|---|---|
| 6,828,440 B2 | 12/2004 | Goehring et al. | |
| 7,504,506 B2 | 3/2009 | Distefano et al. | |
| 7,517,910 B2 | 4/2009 | Yasuma et al. | |
| 7,582,803 B2 | 9/2009 | Akerman et al. | |
| 2006/0183904 A1 | 8/2006 | Guo et al. | |
| 2009/0163527 A1 | 6/2009 | Costanzo et al. | |
| 2009/0170908 A1 | 7/2009 | Shimada et al. | |

FOREIGN PATENT DOCUMENTS

| | | |
|---|---|---|
| EP | 1731505 | 12/2006 |
| WO | 2005/051890 | 6/2005 |
| WO | 2005/086661 | 9/2005 |
| WO | 2008/030618 | 3/2008 |
| WO | 2011066183 | 6/2011 |

OTHER PUBLICATIONS

Diabetes Mellitus, types of Diabetes Mellisa Conrad, Jun. 15, 2012.*
GPR-40, Thierry Alquier et al, May 2009.*
Diabetes, GPR-40 no longer an Orphan, The signalling gateway, Jun. 15, 2012.*

* cited by examiner

*Primary Examiner* — Rita Desai
(74) *Attorney, Agent, or Firm* — MaCharri R Vorndran-Jones

(57) ABSTRACT

A compound of the formula:

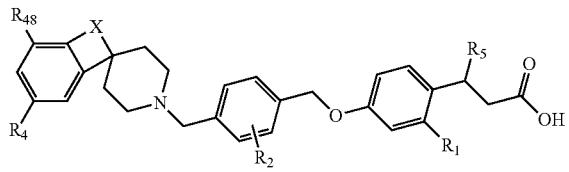

or a pharmaceutically acceptable salt thereof as well as a pharmaceutical composition, and a method for treating diabetes.

25 Claims, No Drawings

SPIROPIPERIDINE COMPOUNDS

This application claims the benefit of U.S. provisional patent applications Ser. Nos. 60/251,839 and 60/303,334, filed 15 Oct. 2009 and 22 Feb. 2010, respectively, and hereby incorporated by reference in their entirety.

Diabetes is one of the most serious health care problems facing the developing world. Some successful commercially available oral treatments for type two diabetes (T2D) are believed to act through modulation of the PPAR gamma receptor.

Administration of these medicines has been associated with undesired adverse effects that sometimes include hypoglycemia, liver damage, gastrointestinal disease, weight gain, or other undesired effects that may be associated with the PPAR gamma activity. New treatment options offering a more desirable safety profile for managing T2D are desired to effectively treat or prevent diabetes in more patients. In particular, novel mechanism-based treatment methods that may minimize or avoid effects that have been associated with PPAR gamma activation are especially desired.

GPR40 is a G protein-coupled receptor which is reported as predominately expressed at high levels in rodent pancreatic beta cells, insulinoma cell lines, and human islets. This receptor is activated by medium and long-chain fatty acids, and thus the receptor is also known as FFAR1 (Free Fatty Acid Receptor 1). See, Briscoe C P et al. *The orphan G protein-coupled receptor GPR40 is activated by medium and long chain fatty acids*, Journal Biological Chemistry 278: 11303-11311, 2003. The glucose dependency of insulin secretion is an important feature of activating GPR40, making this receptor an excellent target for developing efficacious therapies with a desired safety profile for use in the treatment of T2D. Such compounds offer efficacy and a more desirable safety profile as compared to existing therapies such as insulin and sulfonylureas can be especially desirable.

A recently published US Patent application, US 2009/0170908 A1 ("'908"), generally discloses compounds having a hydrocarbon spiro group feature and are stated to have activity as G protein-coupled receptor 40 ("GPR-40") modulators. However, the '908 disclosure does not mention selectivity against PPAR gamma Additionally, the compounds of the '908 disclosure are compounds requiring a hydrocarbon spiro group that is free of heteroatoms in the spiro feature. In contrast, many of the presently claimed spiropiperidine compounds provide desired selective activation of GPR40 without detectable PPAR activity.

Compounds of this invention are potent activators of GPR-40. This invention provides a desired novel treatment option acting through a pharmacological mechanism that is unique compared to commercially available treatments and further provides compounds that selectively activate GPR-40 as compared to PPAR gamma. The pharmacological profile of compounds of this invention, as selective GPR-40 activators, can be particularly desirable for use in the treatment of T2D. Additionally, the selective GPR-40 modulation may provide a particularly desirable safety profile for use in the treatment of T2D by avoiding effects associated with PPAR gamma modulation.

The present invention is directed to compounds of the formula:

I or a pharmaceutically acceptable salt thereof;

wherein:
$R_1$ is selected from the group consisting of H, F and Cl;
$R_2$ is selected from the group consisting of H, $C_{1-3}$alkyl, $CF_3$, $OCH_3$, F, and Cl;
$R_4$ and $R_{4a}$ are each independently selected from the group consisting of H, $OCH_3$, $C_{1-3}$alkyl, $CF_3$, and F, wherein at least one selected from the group consisting of $R_4$ and $R_{4a}$ is H;
$R_5$ is H or C≡CCH$_3$;
X is selected from the group consisting of —CH($R_3$)CH$_2$—, —C($R_3$)=CH—, —N($R_7$)CH$_2$—. and —C(O)CH$_2$—;
$R_3$ is selected from the group consisting of H and $C_{1-3}$ alkyl; and
$R_7$ is selected from the group consisting of H, $C_{1-3}$ alkyl, and phenyl.

The present invention provides an intermediate compound of the formula:

II or a salt thereof;
wherein:
$R_1$ is selected from the group consisting of H, F and Cl;
$R_2$ is selected from the group consisting of H, $C_{1-3}$alkyl, $CF_3$, $OCH_3$, F, and Cl;
$R_4$ and $R_{4a}$ are each independently selected from the group consisting of H, $OCH_3$, $C_{1-3}$alkyl, $CF_3$, and F, wherein at least one selected from the group consisting of $R_4$ and $R_{4a}$ is H;
$R_5$ is H or C≡CH$_3$;
$R_6$ is selected from the group consisting of $C_{1-3}$ alkyl;
X is selected from the group consisting of —CH($R_3$)CH$_2$—, —C($R_3$)=CH—, —N($R_7$)CH$_2$—. and —C(O)CH$_2$—;
$R_3$ is selected from the group consisting of H and $C_{1-3}$alkyl; and
$R_7$ is selected from the group consisting of H, $C_{1-3}$alkyl, $C(O)OC_{1-4}$alkyl, and phenyl.

Compounds of Formula II, wherein $R_6$ is selected from the group consisting of $C_1$-$C_3$ alkyl are useful as intermediates in the synthesis of the spiropiperidine compounds.

A further embodiment of this invention provides the use of a compound as claimed by the present invention or a pharmaceutically acceptable salt thereof for use in the manufacture of a medicament. Another embodiment of the invention is wherein the medicament is for use in the treatment of diabetes. A further embodiment of this invention is the use of a compound as claimed herein or a pharmaceutically acceptable salt thereof for use as a therapy. A further embodiment of the invention is a compound as claimed by the present invention, or a pharmaceutically acceptable salt thereof for use in the treatment of diabetes. Further, the invention relates to a compound as claimed by the present invention for use as a medicament.

A further embodiment of this invention provides a method for treating diabetes in a mammal, comprising the step of administering to the mammal a compound as claimed by the present invention or a pharmaceutically acceptable salt thereof.

In another embodiment, the present invention also relates to pharmaceutical compositions comprising a compound as claimed by the present invention, or a pharmaceutically acceptable salt thereof, and a pharmaceutically acceptable carrier. A further embodiment is a pharmaceutical composition of the present invention further comprising a second pharmaceutical agent.

It is preferred that compounds of this invention selectively activate GPR-40. Relative IC50s for PPAR activity of exemplified compounds are generally greater than 10 uM, supporting that such compound does not activate PPAR isoforms.

The compound of Example 1, (3S)-3-(4-{[4-(1'H-Spiro[indene-1,4'-piperidin]-1'-ylmethyl)benzyl]oxy}phenyl)hex-4-ynoic acid, or a salt thereof may be preferred.

The compound of Example 24, (3S)-3-[4-({4-[(1-Methyl-1,2-dihydro-1'H-Spiro[indole-3,4'-piperidin]-1'-yl)methyl]benzyl}oxy)phenyl]hex-4-ynoic acid, or a salt thereof may be preferred.

When $R_5$ is $C\equiv CCH_3$ compounds of Formula I have a chiral center. The present invention contemplates both the racemic compounds as well as individual isomeric forms. When $R_5$ is $C\equiv CCH_3$ then the S isomer is generally preferred.

Compounds of Formula I wherein $R_5$ is $C\equiv CCH_3$ can be preferred. Compounds wherein $R_5$ is H and $R_1$ is F or Cl can be preferred. Compounds wherein $R_5$ is H and $R_1$ is F may be preferred. Compounds wherein $R_5$ is $C\equiv CCH_3$ and $R_1$ is H can be preferred. Compounds wherein $R_1$ is H can be preferred. Compounds wherein X is selected from the group consisting of $-C(R_3)=CH-$, $-CH(R_3)CH_2-$ and $-N(R_7)CH_2-$ are preferred. Compounds wherein X is $-C(R_3)=CH-$ can be preferred. Compounds wherein $R_3$ is selected from the group consisting of H and $CH_3$ are preferred. Compounds wherein $R_3$ is H may be preferred. Compounds wherein $R_{4a}$ is H are preferred. Compounds wherein $R_2$ is selected from the group consisting of H, $OCH_3$, $CH_3$, and $CF_3$ are preferred. Compounds wherein $R_2$ is H can be preferred. Compounds wherein $R_4$ is selected from the group consisting of H, $OCH_3$, $CH_3$, $CF_3$, and F are preferred. Compounds wherein $R_4$ is selected from the group consisting of $OCH_3$, $CH_3$, $CF_3$, and F can be preferred. Compounds wherein $R_4$ is H can be preferred. Compounds wherein $R_{4a}$ is selected from the group consisting of H and Cl can be preferred. Compounds wherein $R_4$ and $R_{4a}$ are each H can be preferred. Compounds wherein X is $-N(R_7)CH_2-$ can be preferred. Compounds wherein $R_7$ is selected from the group consisting of H and $C_1$-$C_3$ alkyl are preferred. Compounds wherein $R_7$ is $CH_3$ can be especially preferred.

Compounds of Formula II wherein $R_5$ is $C\equiv CCH_3$ can be preferred.

Compounds of Formula II wherein $R_1$ is selected from the group consisting of F and Cl and $R_5$ is H can be preferred.

Compounds of Formula I or a pharmaceutically acceptable salt thereof, wherein:
$R_1$ is H; $R_4$ and $R_{4a}$ are each H; $R_5$ is $C\equiv CCH_3$; $-X$ is $-C(R_3)=CH-$, and $R_3$ is H may be preferred.

Compounds of Formula I or a pharmaceutically acceptable salt thereof, wherein:
$R_1$ is F or Cl; $R_4$ and $R_{4a}$ are each H; $R_5$ is H; X is $-C(R_3)=CH-$ can be preferred.

Compounds of Formula I or a pharmaceutically acceptable salt thereof, wherein:
$R_1$ is F or Cl; $R_4$ and $R_{4a}$ are each H; $R_5$ is $C\equiv CCH_3$; X is $C(R_3)=CH-$ can be preferred.

Compounds of Formula I or a pharmaceutically acceptable salt thereof, wherein:
$R_1$ is F or Cl when $R_5$ is H; $R_1$ is selected from H, F and Cl when $R_5$ is $C\equiv CCH_3$; $R_4$ and $R_{4a}$ are each H; $R_2$ is $CF_3$; X is $-C(R_3)=CH-$, and $R_3$ is H can be preferred.

Compounds of Formula I or a pharmaceutically acceptable salt thereof, wherein:
$R_1$ is F or Cl when $R_5$ is H; $R_1$ is selected from H, F and Cl when $R_5$ is $C\equiv CCH_3$; $R_4$ and $R_{4a}$ are each H; $R_2$ is $CF_3$; and X is $-CH(R_3)CH_2-$ can be preferred.

Compounds of Formula I or a pharmaceutically acceptable salt thereof, wherein:
$R_1$ is F or Cl when $R_5$ is H; $R_1$ is selected from H, F and Cl when $R_5$ is $C\equiv CCH_3$; $R_2$ is selected from the group consisting of $CH_3$, $CF_3$, $OCH_3$, and F; $R_4$ is H; $R_5$ is H or $C\equiv CCH_3$; and X is $-N(R_7)CH_2-$ can be preferred.

Compounds useful as intermediates of Formula II or a pharmaceutically acceptable salt thereof wherein
$R_1$ is F or Cl when $R_5$ is H; $R_1$ is selected from H, F and Cl when $R_5$ is $C\equiv CCH_3$; $R_2$ is selected from the group consisting of $CH_3$, $CF_3$, $OCH_3$, F, and Cl; $R_4$ is selected from the group consisting of H, $OCH_3$, $CH_3$, $CF_3$, and F; $R_5$ is H or $C\equiv CCH_3$; $R_6$ is $C_{1-3}$ alkyl; X is $-N(R_7)CH_2-$, and $R_7$ is $C(O)OC_4$alkyl can be preferred.

Compounds of Formula I or a pharmaceutically acceptable salt thereof, wherein:
$R_1$ is F or Cl when $R_5$ is H; $R_1$ is H when $R_5$ is $C\equiv CCH_3$; $R_2$ is selected from the group consisting of $CH_3$, $CF_3$, $OCH_3$, and F; $R_4$ and $R_{4a}$ are each H; $R_5$ is H or $C\equiv CCH_3$; and X is $-N(R_7)CH_2-$ can be preferred.

Compounds of Formula I or a pharmaceutically acceptable salt thereof, wherein:
$R_1$ is F or Cl when $R_5$ is H; $R_1$ is selected from H when $R_5$ is $C\equiv CCH_3$; $R_2$ is H; $R_4$ is selected from the group consisting of $OCH_3$, $CH_3$, $CF_3$, and F; $R_5$ is H or $C\equiv CCH_3$; and X is $-N(R_7)CH_2-$ can be preferred.

Compounds of Formula I or a pharmaceutically acceptable salt thereof, wherein:
$R_1$ is F or Cl when $R_5$ is H; $R_1$ is selected from H when $R_5$ is $C\equiv CCH_3$; $R_2$ is H; $R_4$ is selected from the group consisting of H, $OCH_3$, $CH_3$, $CF_3$, and F; $R_5$ is H or $C\equiv CCH_3$; X is $-N(R_7)CH_2-$; and $R_7$ is $CH_3$ can be preferred.

The S-isomer of the compound of Formula I wherein $R_5$ is $C\equiv CCH_3$ is generally preferred. The S-isomer of compounds of this invention are generally preferred.

The compounds of the present invention are preferably formulated as a pharmaceutical composition administered by a variety of routes. Most preferably, such compositions are for oral administration. Such pharmaceutical compositions and processes for preparing same are well known in the art. See, e.g., Remington: The Science and Practice of Pharmacy (A. Gennaro, et al., eds., 21st ed., Mack Publishing Co., 2005).

"Pharmaceutically-acceptable salt" refers to salts of the compounds of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The term "pharmaceutically acceptable carrier" means that the carrier, diluent, excipients, and salt are pharmaceutically compatible with the other ingredients of the composition.

Certain stereochemical centers have been left unspecified and certain substituents have been eliminated in the following schemes for the sake of clarity and are not intended to limit the teaching of the schemes in any way. Furthermore, individual isomers, enantiomers, or diastereomers may be separated at any convenient point in the synthesis of compounds of Formula I by methods such as chiral chromatography. Additionally, the intermediates described in the following schemes contain a number of nitrogen, hydroxy, and acid protecting groups. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, (T. Greene and P. Wuts, eds., 2d ed. 1991).

The abbreviations used herein are defined according to *Aldrichimica Acta*, Vol. 17, No. 1, 1984. Other abbreviations are defined as follows: "Prep" refers to preparation; "Ex" refers to example; "min" refers to minute or minutes; "ACN" refers to acetonitrile; "ADDP" refers to 1,1'-(azodicarbonyl) dipiperidine; "boc" or "t-boc" refers to tert butoxycarbonyl; "DCM" refers to dichloromethane; "Et$_2$O" refers to diethyl ether; "EtOAc" refers to ethyl acetate; "EtOH" refers to ethyl alcohol or ethanol; "IPA" refers to isopropyl alcohol; "MeOH" refers to methyl alcohol or methanol; "TFA" refers to trifluoroacetic acid; "THF" refers to tetrahydrofuran; "T$_R$" refers to retention time; "IC$_{50}$" refers to the concentration of an agent that produces 50% of the maximal inhibitory response possible for that agent; "DMEM" refers to Dulbecco's Modified Eagle's Medium; "DTT" refers to dithiothreitol; "F12" refers to Ham's F12 medium; "FBS" refers to Fetal Bovine Serum; "HEK" refers to human embryonic kidney; "PPAR" refers to peroxisome proliferator-activated receptor; "PPRE" refers to peroxisome proliferator response element; "RPMI" refers to Roswell Park Memorial Institute; "TK" refers to thymidine kinase, "RFU" refers to relative fluorescence unit; and "ESI" refers to electrospray ionization.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

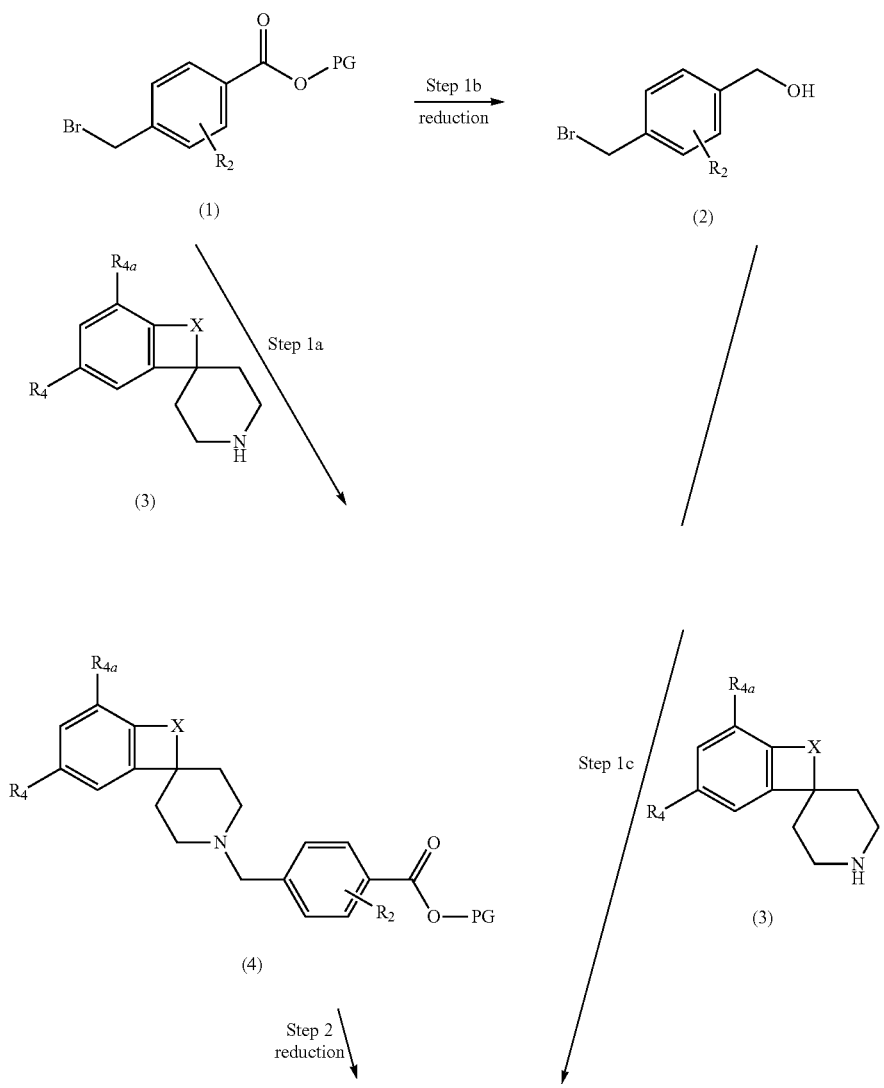

-continued

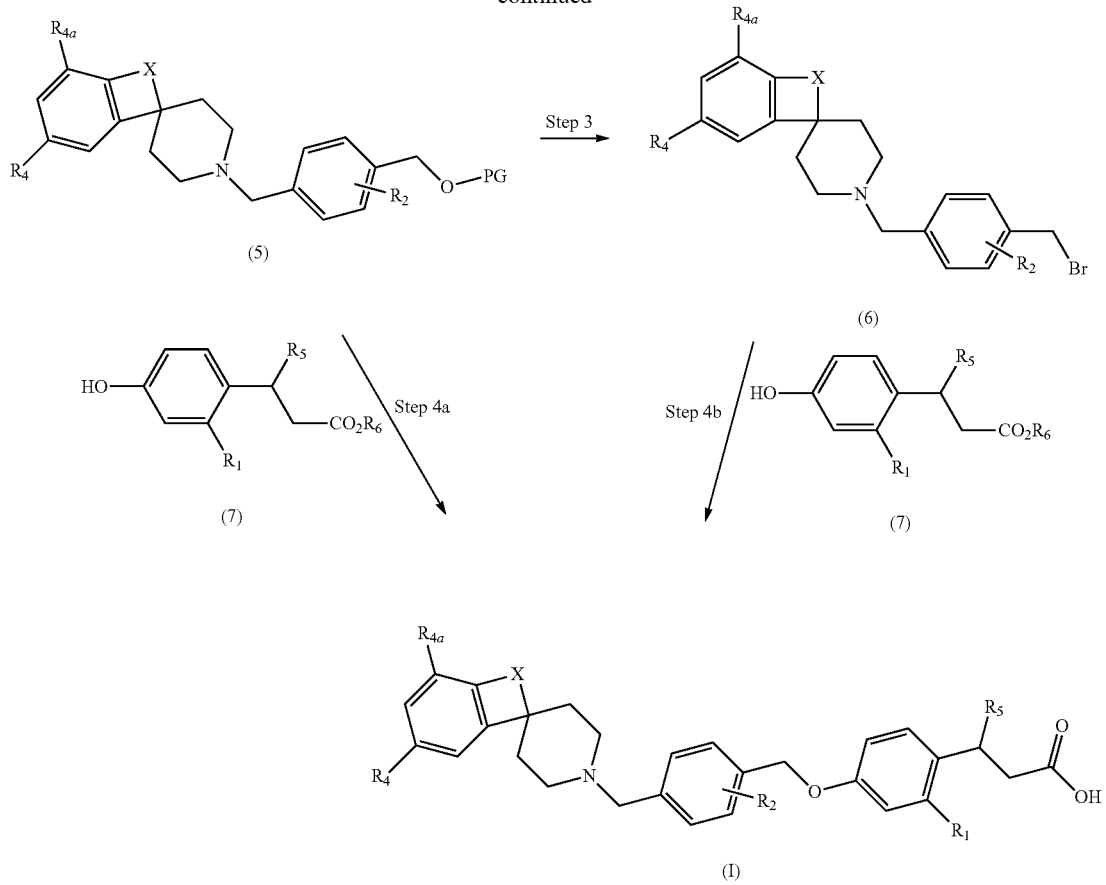

PG = Protecting Group

A compound of Formula I can be prepared in accordance with reactions as depicted in Scheme I. Scheme I (Step 1a) depicts the alkylation of a substituted benzyl bromide (1) with an appropriate substituted piperidine (3) to give, after reduction of the ester in Step 2, a substituted benzyl alcohol (5). Compound (5) can be further extended at the hydroxyl to give compounds of Formula I or compounds can be further deprotected to give compounds of Formula I. "PG" is a protecting group developed for an acid such as esters and also for an amino group such as carbamates and amides. Such protecting groups are well known and appreciated in the art. See. e.g., Greene and Wuts, *Protective Groups in Organic Synthesis*, supra.

A compound of formula (1) is reacted with a compound of formula (3) under alkylation conditions (Step 1a). One skilled in the art will recognize that there are a number of methods and reagents for amine alkylation resulting from the reaction of benzyl bromides and amines. For example, the reaction of an appropriate compound of formula (1) with an appropriate amine or amine salt such as trifluoroacetic acid salt or HCl salt of formula (3) in the presence of a base such as diisopropylethylamine or cesium carbonate will give a compound of formula (4). The carbonyl of the ester of formula 4 can be reduced as in Step 2 using a reducing agent such as diisobutylaluminum hydride, lithium aluminum hydride or sodium borohydride to give compound (5). Compound (5) can then be further alkylated with compounds of formula (7) under Mitsunobu conditions to give compounds of Formula (I). Mitsunobu conditions are well known in the art and involve reacting an alcohol (5) with a nucleophile such as a phenol (7) using a phosphine such as tributyl phosphine, triphenyl phosphine, or triethylphosphine and an azodicarbonyl such as ADDP or an azodicarboxylate such as diethyl azodicarboxylate (DEAD). Alternatively, compound 5 can be converted to a benzyl bromide (6, Step 3) using an appropriate brominating agent such as phosphorus tribromide. Compound (6) can be alkylated in Step 4b with (7) using an appropriate base such as potassium carbonate and deprotected if necessary to give compounds of Formula I. In another variation, a compound of formula (1) can be reduced to the bromo benzyl hydroxy (2), as shown in Step 1b using a reducing agent such as diisobutyl aluminum hydride or compound (2) may be available commercially and alkylated with an appropriate amine or amine salt of formula (3, Step 1c) in the presence of a base such as diisopropylethylamine or cesium carbonate to give compound (5) and then carried on as described above to give compounds of Formula (I).

In an optional step, a pharmaceutically acceptable salt of a compound of Formula (I) can be formed by reaction of an appropriate acid of Formula (I) with an appropriately pharmaceutically acceptable base in a suitable solvent under standard conditions. Additionally, the formation of such salts can occur simultaneously upon hydrolysis of an ester. The formation of such salts is well known and appreciated in the art.

Scheme II

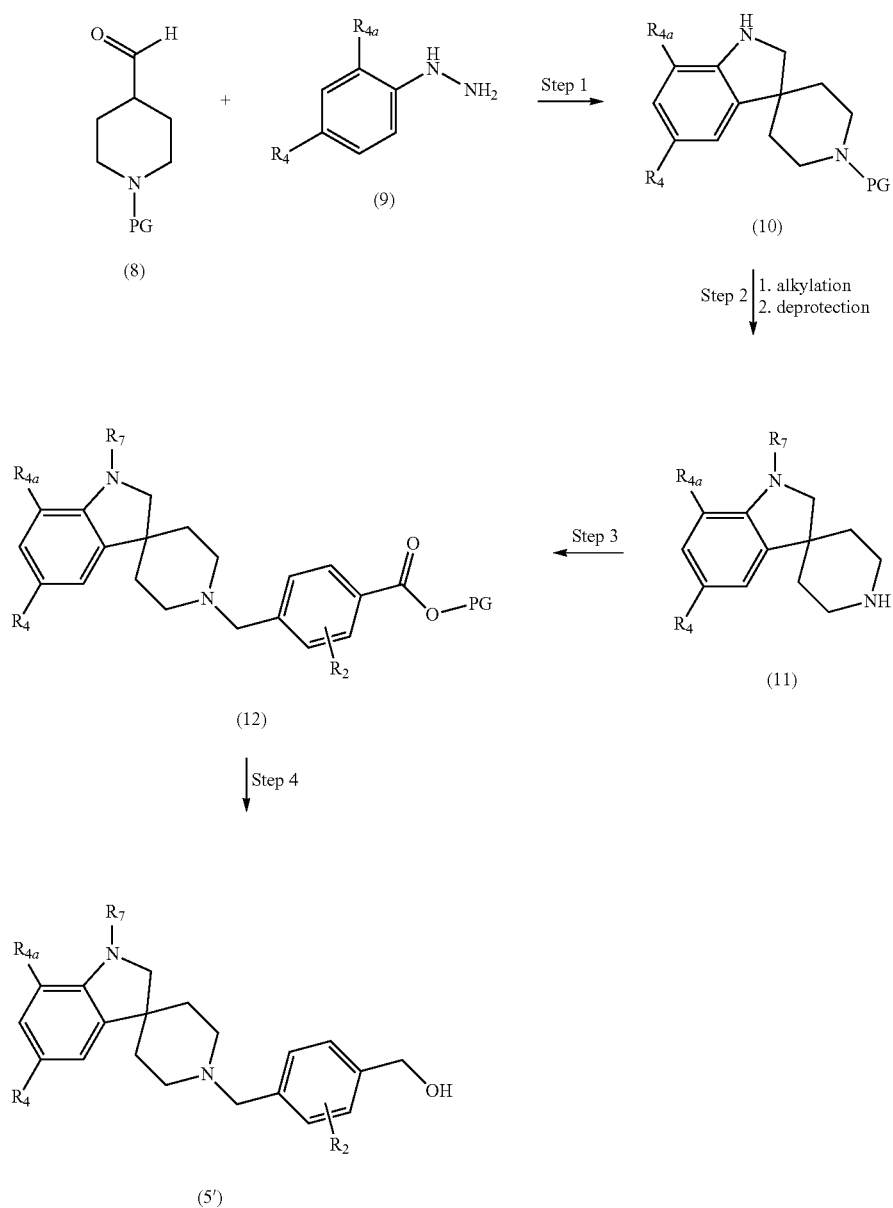

In Scheme II, Step 1, a protected piperidine-4-carboxaldehyde (8) is reacted with a substituted phenylhydrazine (9) in an acid catalyzed cyclization to give a substituted spiro[indoline-3,4'-piperidine] (10) which can then be alkylated and deprotected and further alkylated to give compounds of Formula (I). For example, to phenyl hydrazine (9) or a substituted phenyl hydrazine (9) and an appropriate acid such as trifluoroacetic acid is added a nitrogen protected-4-formyl-piperidine (8). After an appropriate reaction time, a reducing agent such as sodium borohydride and an alcohol such as methanol is added to give the desired substituted spiro{indoine-3,4'-protected piperidine] (10). In Step 2, the indoline nitrogen of (10) can be alkylated by reductive alkylation using an appropriate aldehyde and an appropriate reducing agent such as sodium cyanoborohydride in an appropriate acid such as acetic acid and an alcohol such as methanol. Following deprotection, compound (11) can be isolated. Alternatively, the indoline amine (10) can be protected with a protecting group such as boc using di-tert-butyldicarbonate or the indoline amine can be alkylated under standard conditions using an alkylating agent such as bromobenzene, and an appropriate base such as cesium carbonate. Following deprotection of the piperidine nitrogen compound (11) can be isolated. The protecting group on the piperidine nitrogen can be removed under standard conditions well known in the art such as hydrogenation or acidic conditions to give compound (11). Compound (11), in Step 3 can then be alkylated with (1) as previously described to give compound (12) and reduced in Step 4 as previously described in Scheme I, (steps 1a and 2) to give compound (5'). Compound (5') can then be carried on to give compounds of Formula (I) as described for Scheme I substantially the same as compound (5).

Scheme III

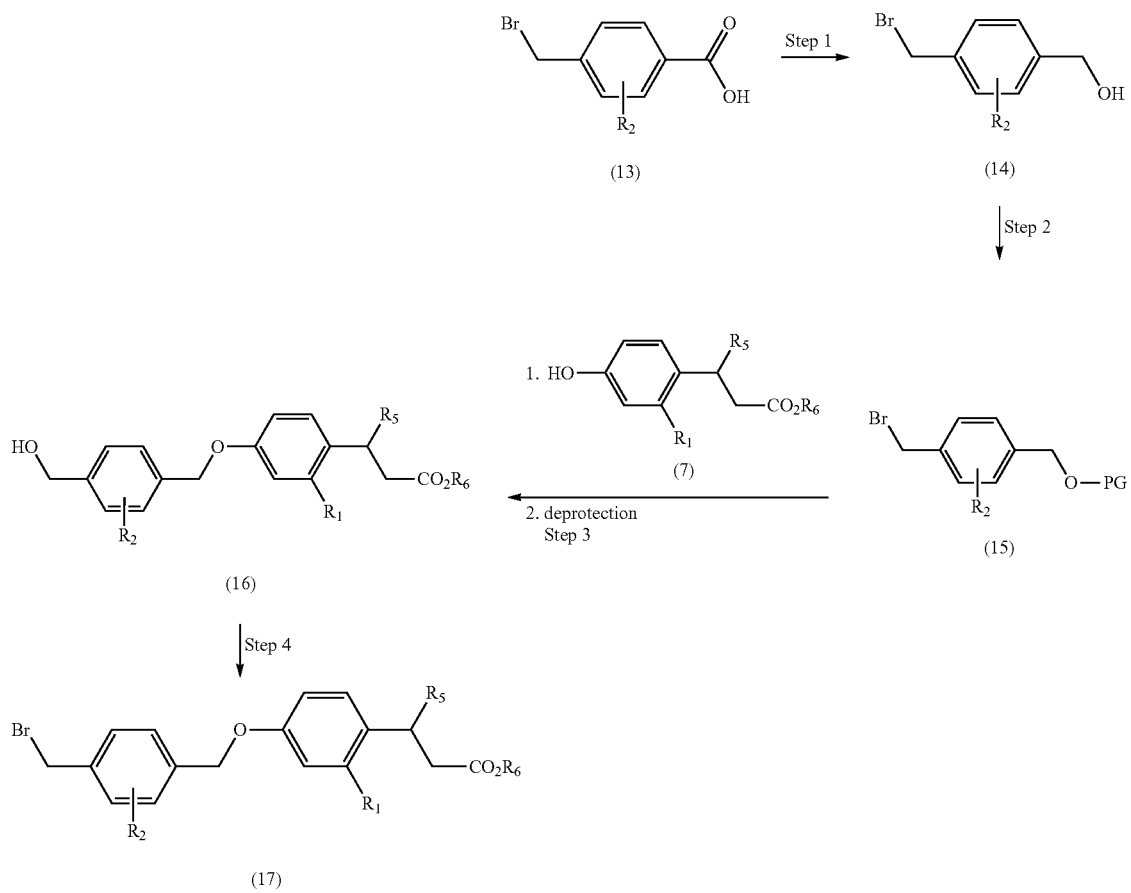

In Scheme III a substituted benzoic acid is reduced under conditions well known in the art using a reducing agent such as DIBAL-H to give compound (14) in Step 1. In Step 2, the hydroxyl compound (14) can be protected with a protecting group such as tert-butyl-dimethyl silane using a base such as imidazole and tert-butylchlorodimethylsilane to give (15). Compound (15) can be alkylated with compound (7) using a base such as potassium carbonate and deprotected to give compound (16) in Step 3. The hydroxyl of compound (16) can be converted to the bromide using brominating conditions such as phosphorus tribromide to give compound (17) in Step 4. Compound (17) can then be alkylated with compound (3, Scheme I) under conditions well known in the art with a base such as cesium carbonate or N,N-diisopropylethylamine and deprotected to give compounds of Formula (I).

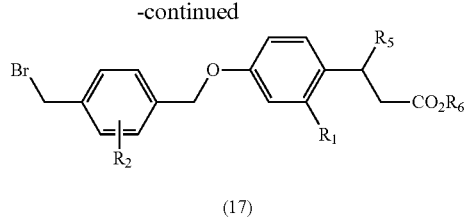

Scheme IV

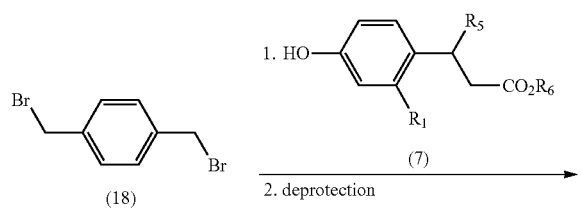

Alternatively as shown in Scheme IV, 1,4-bis(bromomethyl)benzene (18) can be monoalkylated with compound (7) using a base such as cesium carbonate to give compound (17). Compound (17) can then be alkylated with compound (3, Scheme I) under conditions well known in the art with a base such as cesium carbonate or N,N-diisopropylethylamine and deprotected to give compounds of Formula (I).

Scheme V

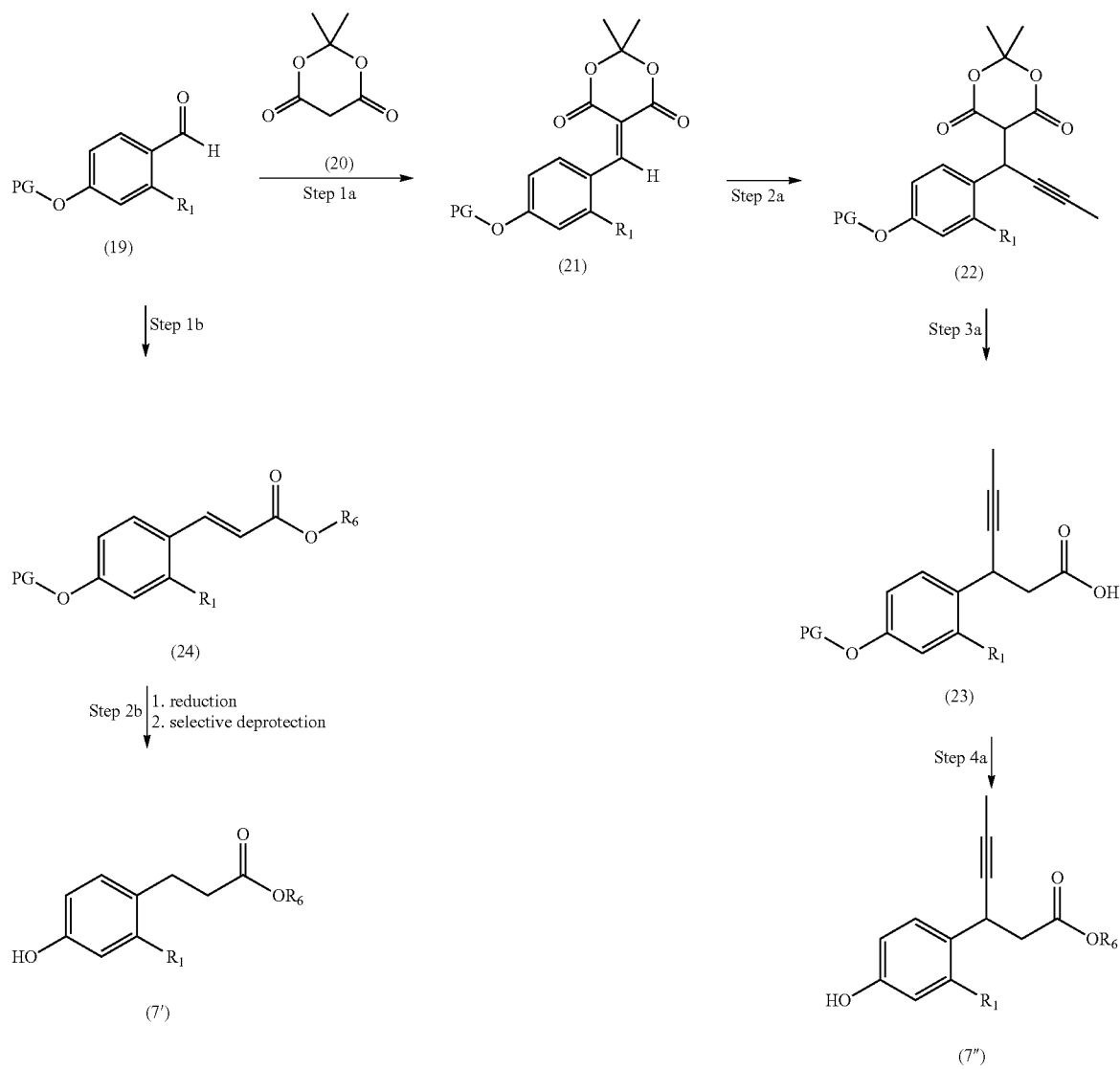

There are various methods to build components of compounds of Formula (I) that are well known in the art. As shown in Scheme V, one example is to protect the aldehyde of a substituted benzaldehyde (19) for example using Meldrum's acid (2,2-dimethyl-1,3-dioxane-4,6-dione), (20), in a Knoevenagel condensation to give (21) in Step 1a. Aldehydes can be commercially purchased or prepared by standard methods well known in the art. The benzaldehyde (19) can be substituted with a hydroxyl or the hydroxyl can be protected by protecting groups well known in the art. A Grignard reaction can then be accomplished using a typical Grignard reagent such as 1-propynyl magnesium bromide to give (22, Step 2a). Deprotection of the Meldrum's acid intermediate (22) with a base such as pyridine-water and an acid work-up gives compound (23, Step 3a), a carboxylic acid. The protected hydroxyl can be deprotected using borontribromide and the acid can be protected to give (7", Step 4a) when $R_5$ is C≡CCH$_3$. It should be noted that a chiral separation can be accomplished at various steps in the process such as at Step 3a. Compound (7") can then be used as in Scheme I substantially the same as compound (7) to give compounds of Formula (I).

Alternatively, a hydroxyl protected benzaldehyde (19) can be reacted with a phosphonium salt such as triethyl phosphoacetate and a base such as sodium hydride to form a Wittig reagent to give the ethyl protected acrylate (24, Step 1b). The double bond can be reduced under hydrogenation conditions using a typical catalyst such as 10% Pd/C and hydrogen and followed by deprotection of the hydroxyl using borontribromide to give compound (7') in Step 2b. Compound (7') can then be used as in Scheme I substantially the same as compound (7) to give compounds of Formula (I).

PREPARATIONS AND EXAMPLES

The following preparations and examples further illustrate the invention and represent typical synthesis of the compounds of Formula (I). The names for the compounds of the present invention are generally provided by IUPACNAME ACDLABS and Symyx Draw 3.2.

Preparation 1

Benzyl spiro[indoline-3,4'-piperidine]-1'-carboxylate

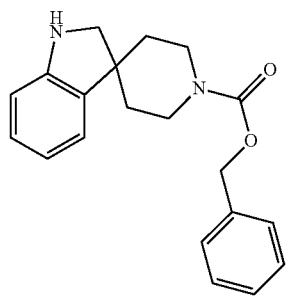 [SMILES: O=C(OCc1ccccc1)N1CCC2(CC1)CNc1ccccc12]

A solution of phenyl hydrazine (1.29 g, 12.0 mmol) and trifluoroacetic acid (3.0 mL) in a 49:1 solution of toluene: acetonitrile (50 mL) is heated at 35° C. 4-Formyl-piperidine-1-carboxylic acid benzyl ester (2.7 g, 10.91 mmol) is dissolved in a 49:1 solution of toluene:acetonitrile (10 mL) and added dropwise to the mixture (WO2005046682). The mixture is stirred at 35° C. overnight. The resulting solution is cooled to 0° C., and methanol (5 mL) is added. NaBH$_4$ (0.619 g, 16.38 mmol) is added portion wise to the solution and the mixture is stirred for 45 min. The reaction mixture is washed with aqueous NH$_4$OH (6%, 25 mL) and brine (30 mL), dried over sodium sulfate, and evaporated to dryness to give a yellow solid. The crude solid is recrystallised from EtOAc to give a yellow solid (1.25 g, $1^{st}$ crop). The mother liquor is evaporated and purified by silica gel chromatography, eluting with hexane:ethyl acetate (8:2) to give the title compound as a pale yellow solid (1.2 g, $2^{nd}$ crop) with a total yield of (2.4 g, 76%). ESI/MS m/z 323 (M+H)$^+$.

The following compounds are prepared essentially as described by the method of preparation 1.

| Prep. No. | Chemical Name | ESI/MS (m/z) (M + H) |
|---|---|---|
| 2 | Benzyl 5-(trifluoromethylspiro[indoline-3,4'-piperidine]-1'-carboxylate | 391 |
| 3 | Benzyl 7-chlorospiro[indoline-3,4'-piperidine]-1'-carboxylate | 357 |
| 4 | Benzyl 5-fluorospiro[indoline-3,4'-piperidine]-1'-carboxylate | 341 |
| 5 | Benzyl 5-methoxyspiro[indoline-3,4'-piperidine]-1'-carboxylate | 353 |
| 6 | Benzyl 5-methylspiro[indoline-3,4'-piperidine]-1'-carboxylate | 337 |

Preparation 7

Benzyl 1-methylspiro[indoline-3,4'-piperidine]-1'-carboxylate

To a 0° C. solution of benzyl spiro[indoline-3,4'-piperidine]-1'-carboxylate (1.15 g, 3.56 mmol), formaldehyde (37% aqueous solution, 1.44 mL, 17.83 mmol) and acetic acid (1.02 mL, 17.83 mmol) in methanol (25 mL) is added sodium cyanoborohydride (0.67 g, 10.68 mmol). The reaction mixture is allowed to warm to room temperature overnight. The pH of the mixture is adjusted to approximately 8 with 10% NaHCO$_3$ solution and extracted with EtOAc (3×50 mL). The combined extracts are washed with water (50 mL) and brine (50 mL), dried, filtered, and evaporated to dryness. The crude material is purified by silica gel chromatography, eluting with hexane:ethyl acetate (85:15) to give the title compound as an off-white solid (0.9 g, 75%). ESI/MS m/z 337.2 (M+H)$^+$.

The following compounds are prepared essentially as described by the method of preparation 7 using an appropriate aldehyde.

| Prep. No. | Chemical Name | ESI/MS (m/z) (M + H) |
|---|---|---|
| 8 | Benzyl 1-methyl-5-(trifluoromethyl)spiro[indoline-3,4'-piperidine]-1'-carboxylate | 405 |
| 9 | Benzyl 7-chloro-1-methyl-spiro[indoline-3,4'-piperidine]-1'-carboxylate | 371 |
| 10 | Benzyl 5-fluoro-1-methyl-spiro[indoline-3,4'-piperidine]-1'-carboxylate | 355 |
| 11 | Benzyl 5-methoxy-1-methyl-spiro[indoline-3,4'-piperidine]-1'-carboxylate | 367 |
| 12 | Benzyl 1,5-dimethyl-dimethylspiro[indoline-3,4'-piperidine]-1'-carboxylate | 351 |
| 13 | Benzyl 1-isopropylspiro[indoline-3,4'-piperidine]-1'-carboxylate | 365 |

Preparation 14

Benzyl 1-phenylspiro[indoline-3,4'-piperidine]-1'-carboxylate

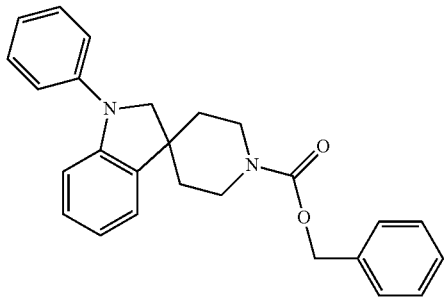 [SMILES: O=C(OCc1ccccc1)N1CCC2(CC1)CN(c1ccccc1)c1ccccc12]

To a solution of benzyl spiro[indoline-3,4'-piperidine]-1'-carboxylate (1.5 g, 4.65 mmol) in 1-4, dioxane (5 mL) is added bromobenzene (0.803 g, 5.115 mmol), 4,5-(diphenylphosphino)-9,9-dimethyl xanthene (0.807 g, 1.395 mmol) and cesium carbonate (4.54 g, 13.95 mmol) at 0° C. The reaction mixture is purged with nitrogen gas for 15 minutes and palladium acetate (0.062 g, 0.279 mmol) is added. The mixture is stirred at 100° C. for 5 hours, filtered, diluted with ammonium chloride solution, extracted with EtOAc, dried with sodium sulphate, and concentrated under reduced pressure. The crude material is purified by silica gel chromatography, eluting with hexane:ethyl acetate (9.0:1.0) to give the title compound (1.6 g, 86.48%). ESI/MS m/z 399.4 (M+H)$^+$.

Preparation 15

1-Methylspiro[indoline-3,4'-piperidine]

To a solution of benzyl 1-methyl spiro[indoline-3,4'-piperidine]-1'-carboxylate (0.85 g, 2.52 mmol) in methanol (50 mL) is added Pd(OH)$_2$/C (10%, 0.15 g) and the mixture is hydrogenated with a balloon for 16 hours. The reaction mixture is filtered through diatomaceous earth, washed with methanol (50 mL), and evaporated to dryness to give the title compound (0.5 g, 98%). EST/MS m/z 203.4 (M+H)$^+$.

The following compounds are prepared essentially as described by the method of preparation 15.

| Prep. No. | Chemical Name | ESI/MS (m/z) (M + H) |
|---|---|---|
| 16 | tert-Butyl spiro[indoline-3,4'-piperidine]-1-carboxylate | 289 |
| 17 | 1-Methyl-5-(trifluoromethyl)-spiro[indoline-3,4'-piperidine] | 270 |
| 18 | 5-Methoxy-1-methyl-spiro[indoline-3,4'-piperidine] | 233 |
| 19 | 1,5-Dimethylspiro[indoline-3,4'-piperidine] | 217 |
| 20 | 1-Isoproylspiro[indoline-3,4'-piperidine] | 231 |
| 21 | 1-Phenylspiro[indoline-3,4'-piperidine] | 265 |

Preparation 22

7-Chloro-1-methyl-spiro[indoline-3,4'-piperidine]

A solution of benzyl 7-chloro-1-methyl-spiro[indoline-3,4'-piperidine]-1'-carboxylate (1.1 g, 2.96 mmol) in trifluoroacetic acid (10 mL) is refluxed for 3 hours. The reaction mixture is concentrated, the pH of the residue is adjusted with 10% NaHCO$_3$ (20 mL) to basic and extracted with EtOAc (3×20 mL). The combined extracts are washed with 10% NaHCO$_3$ (20 mL), water (20 mL), and brine solution (20 mL), dried with a drying agent, filtered, and evaporated to dryness to give the title compound as a brown liquid (0.73 g, 103.9% crude). ESI/MS m/z 237.1 (M+H)$^+$.

Preparation 23

5-[(4-Hydroxyphenyl)methylene]-2,2-dimethyl-1,3-dioxane-4,6-dione

To a solution of 4-hydroxybenzaldehyde (20 g, 163 mmol) in water (250 mL) is added Meldrum's acid (2,2-dimethyl-1,3-dioxane-4,6-dione) (24.78 g, 171 mmol) as a slurry in water (250 mL) at 75° C. The reaction mixture is agitated for 2 hours, cooled in an ice bath, and extracted with EtOAc (2×400 mL). The combined extracts are washed with saturated brine, dried over sodium sulfate, filtered, and concentrated to a yellow solid (39 g, 97%). ESI/MS m/z 247.1 (M−H)$^−$.

The following compound is prepared essentially as described by the method of preparation 23.

| Prep. No. | Chemical Name | ESI/MS (m/z) (M + H) |
|---|---|---|
| 24 | 5-(2-Fluoro-4-methoxy-phenyl)methylene]-2,2-dimethyl-1,3-dioxane-4,6-dione | 280 |

Preparation 25

5-[1-(4-Hydroxyphenyl)but-2-ynyl]-2,2-dimethyl-1,3-dioxane-4,6-dione

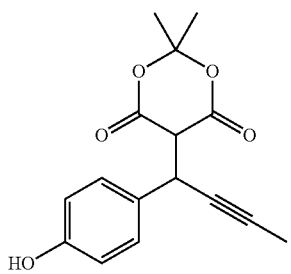 [SMILES: CC#CC(c1ccc(O)cc1)C1C(=O)OC(C)(C)OC1=O]

To a solution of 1-propynyl magnesium bromide in THF (0.5 N, 322 mL, 161.28 mmol) is added a solution of 5-(4-hydroxy-benzylidene)-2,2-dimethyl-[1,3]dioxane-4,6-dione (20 g, 80.64 mmol) in THF (200 mL) by cannula under a nitrogen atmosphere. Over the course of the addition, the reaction mixture changed to a thick, yellow suspension. After addition is compete, the reaction mixture is stirred for 15 minutes at 50° C., quenched with aqueous NH$_4$Cl, and acidified to pH ~2 with 2 N HCl. The mixture is extracted with EtOAc (2×300 mL) and the combined extracts are washed with saturated brine, dried over MgSO$_4$, filtered, and concentrated to a yellow solid (20 g, 86%). The product is carried on crude.

The following compounds are prepared essentially as described by the method of preparation 25.

| Prep. No. | Chemical Name | ESI/MS (m/z) (M + H) |
|---|---|---|
| 26 | 5-[1-(2-Fluoro-4-methoxy-phenyl)but-2-ynyl]-2,2-dimethyl-1,3-dioxane-4,6-dione | 320 |

Preparation 27

3-(4-Hydroxyphenyl)hex-4-ynoic acid

A solution of 5-[1-(4-hydroxyphenyl)but-2-ynyl]-2,2-dimethyl-1,3-dioxane-4,6-dione (20 g, 69.44 mmol) in pyridine-water (5:1, 390 mL) is heated at reflux for 16 hours and after cooling is acidified to pH ~2 with 5 N HCl and extracted with EtOAc (2×300 mL). The combined extracts are washed with saturated brine, dried over MgSO$_4$, filtered, and concentrated to give an off-white solid (13.5 g, 96%). ESI/MS m/z 203 (M−H)$^-$.

The following compounds are prepared essentially as described by the method of preparation 27

| Prep. No. | Chemical Name | ESI/MS (m/z) (M + H) |
|---|---|---|
| 28 | 3-(2-Fluoro-4-methoxy-phenyl)hex-4-ynoic acid | 236 |

Preparation 29

(3S)-3-(4-Hydroxyphenyl)hex-4-ynoic acid 3-(4-Hydroxyphenyl)hex-4-ynoic acid enantiomers are separated by chiral chromatography [column chiralpak IA (250 mm×4.6 mm), mobile phase (A) n-hexane, mobile phase (B) isopropyl alcohol with 0.01% TFA; composition (85:15), flow rate 1.0 mL/min, detection 225 nm) to give the title compound, (4.2 g, 50.58%) retention time 7.96. ESI/MS m/z 203 (M+H)$^-$. The mixture of enantiomers is also separated by chiral resolution using a similar method as described in WO2005086661 to give the title compound.

Preparation 30

Ethyl (3S)-3-(4-hydroxyphenyl)hex-4-ynoate

To a 0° C. solution of (3S)-3-(4-hydroxyphenyl)hex-4-ynoic acid (2.7 g, 13.2 mmol) in ethanol (135 mL) is added sulfuric acid (2.7 mL) and the mixture is heated at reflux for 4 hours, concentrated, diluted with water, and extracted with EtOAc (2×100 mL). The combined extracts are washed with saturated brine, dried over sodium sulfate, filtered, and concentrated to yellow oil (2.1 g, 68%). $^1$H NMR (400 MHz, CDCl$_3$) δ 7.23 (d, J=8.0 Hz, 2H), 6.76 (d, J=8.0 Hz, 2H), 4.9 (bs, 1H), 4.11 (q, J=6.8 Hz, 2H), 4.04 (m, 1H), 2.60-2.75 (m, 2H), 1.82 (s, 3H), 1.21 (t, J=6.8 Hz, 3H).

The following compounds are prepared essentially as described by the method of preparation 30

| Prep. No. | Chemical Name | ESI/MS (m/z) (M + H) |
|---|---|---|
| 31 | Ethyl 3-(4-hydroxyphenyl)hex-4-ynoate | a |
| 32b | Methyl 3-(2-fluoro-4-hydroxy-phenyl)hex-4-ynoate, isomer 1 | 236 | a. $^1$H NMR (400 MHz, DMSO-d6) δ 9.25 (s, 1H), 7.01 (d, J = 8.4 Hz, 2H), 6.65 (d, J = 8.4 Hz, 2H), 3.97-4.02 (m, 2H), 3.9 (m, 1H), 2.59 (d, J = 7.6 Hz, 1H), 2.46 (m, 1H), 1.7 (s, 3H), 1.09 (t, J = 7.6 Hz, 3H).
32b. Methyl 3-(2-fluoro-4-hydroxy-phenyl)hex-4-ynoate is separated by chiral HPLC (Chiralpak IA, flow rate 0.6 mL/min, detection 225 nm, 90:10 heptane:IPA) to give methyl 3-(2-fluoro-4-hydroxy-phenyl)hex-4-ynoate, Isomer-1.

Preparation 33

3-(2-Fluoro-4-hydroxy-phenyl)hex-4-ynoic acid 3-(2-Fluoro-4-methoxy-phenyl)hex-4-ynoic acid (0.250 g, 1.12 mmol) is dissolved in DCM (5 mL) and boron tribromide (0.5 mL, 3.7 mmol) is added at −10° C. The mixture is stirred at ambient temperature for 1 hour. The solution is concentrated under reduced pressure, diluted with water, and extracted with EtOAc, dried with a drying agent, and concentrated under reduced pressure to give the title compound as a pale brown liquid (0.180 g, 76%). ESI/MS m/z 212 (M−H)⁻.

Preparation 34

Ethyl 3-(2-fluoro-4-methox-phenyl)propanoate

A mixture of ethyl (E)-3-(2-fluoro-4-methoxy-phenyl)prop-2-enoate (11 g, 49 mmol) and 10% Pd/C catalyst (1.1 g) in ethanol (120 mL) is stirred overnight under hydrogen atmosphere with a balloon. The mixture is filtered through diatomaceous earth, washed with ethanol and the filtrate is evaporated to dryness to give the title compound (10 g, 90%). ¹H NMR (400 MHz, DMSO-d6) δ 7.17 (t, J=8.8 Hz, 1H), 6.74 (d, J=12.4 Hz, 1H), 6.69 (d, J=8.4 Hz, 1H), 4.02 (q, J=7.2 Hz, 2H), 3.71 (s, 3H), 2.77 (t, J=7.6 Hz, 2H), 2.53 (t, J=7.6 Hz, 2H), 1.13 (t, J=7.2 Hz, 3H).

The following compound is prepared essentially as described by the method of preparation 34

| Prep. No. | Chemical Name | ESI/MS (m/z) (M − H)⁻ |
|---|---|---|
| 35 | Ethyl 3-(2-chloro-4-hydroxy-phenyl)propanoate | 227 |

Preparation 36

[4-(Bromomethyl)phenyl]methanol

To a solution of 4-bromomethyl-benzoic acid methyl ester (5 g, 21.82 mmol) in DCM (200 mL) is added DIBAL-H (1.0 M in hexane, 54.56 mL, 54.56 mmol) drop wise at −78° C. The reaction mixture is allowed to warm to room temperature and stirred for 16 hours. The reaction mixture is quenched with sodium potassium tartrate (10% solution, 8 mL) and diluted with DCM (100 mL). The combined organic layer is washed with water (50 mL), brine (25 mL), dried over sodium sulfate, and evaporated to give the title compound as an off white solid (3.5 g, 81%). ¹H NMR (400 MHz, CDCl₃) δ 7.23-7.21 (m, 2H), 7.4-7.3 (m, 2H), 4.5-4.3 (bs, 2H), 4.68 (s, 2H).

The following compounds are prepared essentially as described by the method of preparation 36.

| Prep. No. | Chemical Name | ESI/MS (m/z) (M + H) |
|---|---|---|
| 37 | [4-(Bromomethyl)-2-methoxyphenyl]methanol | a |
| 38 | (4-Bromo-2-methylphenyl)methanol | 202 | a. ¹H NMR (400 MHz, CDCl₃) 7.25-7.24 (d, J = 4 Hz, 1H), 6.98-6.96 (d, J = 8 Hz, 1H), 6.91 (s, 1H), 4.67 (s, 2H), 4.48 (s, 2H), 3.88 (s, 3H).

Preparation 39

Ethyl (3S)-3-[4-[[4-(bromomethyl)phenyl]methoxy]phenyl]hex-4-ynoate

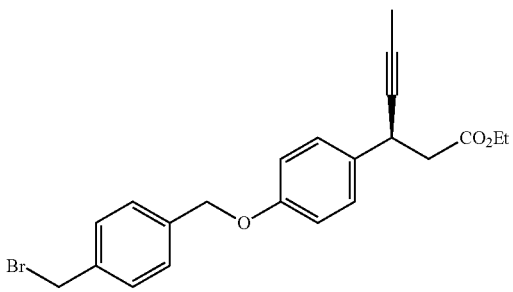 [SMILES: CC#C[C@@H](CC(=O)OCC)c1ccc(OCc2ccc(CBr)cc2)cc1]

To a solution ethyl (3S)-3-(4-hydroxyphenyl)hex-4-ynoate (0.1 g, 0.43 mmol) and 1,4-bis(bromomethyl)benzene (0.227 g, 0.861 mmol) in DMF (5 mL) is added Cs₂CO₃ (0.28 g, 0.861 mmol) at 0° C. The reaction mixture is allowed to warm to room temperature over 2 h. The reaction mixture is diluted with water (25 mL) and extracted with EtOAc (3×10 mL). The combined organic layer is washed with water (10 mL×3) and saturated brine solution (10 mL), dried, filtered, and evaporated to dryness. The crude product is purified by silica gel chromatography, eluting with hexane:ethyl acetate (9.0:1.0) to give the title compound (0.1 g, 55.9%). ESI/MS m/z (M+H)⁺ 415.4.

The following compound is prepared essentially as described by the method of preparation 39

| Prep. No. | Chemical Name | ESI/MS (m/z) (M + H) |
|---|---|---|
| 40 | Ethyl 3-[4-[[4-(bromomethyl)phenyl]methoxy]-2-fluorophenyl]propanoate | a | a. ¹H NMR (400 MHz, CDCl₃) δ 7.42-7.36 (m, 4H), 7.12-7.07 (m, 1H), 6.68-6.3 (m, 2H), 5.01 (s, 2H), 4.50 (s, 2H), 4.10-4.09 (m, 2H), 2.92-2.88 (m, 2H), 2.60-2.58 (m, 2H), 1.24-1.21 (m, 3H).

Preparation 41

Ethyl-4-(spiro[indene-1,4'-piperidine]-1'-ylmethyl)benzoate

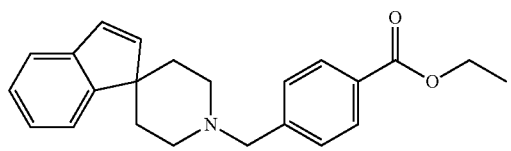 [SMILES: CCOC(=O)c1ccc(CN2CCC3(C=Cc4ccccc43)CC2)cc1]

To a solution of spiro-[indene-1,4-piperidine]trifluoroacetate (4 g, 14 mmol) in ethanol (25 mL) is added ethyl 4-(bromomethyl)-benzoate (2.9 g, 12.6 mmol), followed by diisopropylethylamine (9.6 mL, 56 mmol). The reaction mixture is refluxed at 85° C. for overnight. The ethanol is removed under reduced pressure and the residue is partitioned between EtOAc (150 mL) and water (50 mL). The organic layer is washed with brine, dried over anhydrous sodium sulfate, filtered, and concentrated under reduced pressure. The residue is purified by silica gel chromatography, eluting with hexane:ethyl acetate (8.0:2.0) to give the title compound as brown solid (2.8 g, 60%). $^1$H NMR (400 MHz) 7.94 (d, J=8 Hz, 2H), 7.51 (d, J=8 Hz, 2H), 7.43 (d, J=7.2 Hz, 1H), 7.31 (d, J=7.2 Hz, 2H), 6.94 (d, J=5.6 Hz, 1H), 6.78 (d, J=5.6 Hz, 1H), 4.30 (q, J=7.2 Hz, 2H), 3.67 (s, 2H), 2.85 (d, J=11.6 Hz, 2H), 2.38 (t, J=11.6 Hz, 2H), 2.09 (t, J=10.4 Hz, 2H), 1.31 (t, J=7.2 Hz, 2H), 1.19 (d, J=12.8 Hz, 2H).

The following compounds are prepared essentially as described by the method of preparation 41.

| Prep. No. | Chemical Name | ESI/MS (m/z) (M + H) |
|---|---|---|
| 42 | Ethyl-3-chloro-4-(spiro[indene-1,4'-piperidine]-1'-ylmethyl)benzoate | 382 |
| 43 | Ethyl-2-methoxy-4-spiro[indene-1,4'-piperidine]-1'-ylmethyl)benzoate | 378 |
| 44 | Ethyl-3-fluoro-4-(spiro[indene-1,4'-piperidine]-1'-ylmethyl)benzoate | 366 |
| 45 | Ethyl-4-(spiro[indene-1,4'-piperidin]-1'-ylmethyl)-3-(trifluoromethyl)benzoate | 416 |
| 46 | Ethyl-3-chloro-4-[(1-methylspiro[indoline-3,4'-piperidin]-1'-yl)methyl]benzoate | 399 |
| 47 | Ethyl-4-(spiro[indane-1,4'-piperidin]-1'-ylmethyl)-3-(trifluoromethyl)benzoate | 418 |

Preparation 48

(4-(Spiro[indene-1,4'-piperidine]-1'-ylmethyl)phenyl)methanol

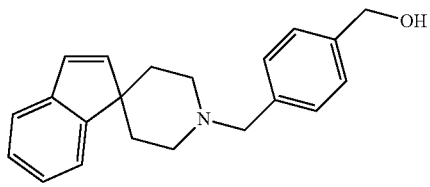 [SMILES: OCc1ccc(CN2CCC3(C=Cc4ccccc43)CC2)cc1]

To a −78° C. solution of ethyl-4-(spiro[indene-1,4'-piperidine]-1-ylmethyl)benzoate (2.8 g, 80 mmol) in DCM (50 mL) is added diisobutylaluminum hydride (1 M in THF, 40 mL, 40 mmol). The mixture is stirred at −78° C. for 2 hours. The reaction is quenched with water (25 mL) and stirred at room temperature for 30 minutes. The reaction mixture is filtered through diatomaceous earth and extracted with DCM (25 mL×2). The combined organic layers are washed with brine, dried over anhydrous sodium sulfate, filtered, and concentrated to give the title compound as a white solid (1.5 g, 46%). $^1$H NMR δ 7.94 (d, J=8 Hz, 2H), 7.51 (d, J=8 Hz, 2H), 7.43 (d, J=7.2 Hz, 1H), 7.31 (d, J=7.2 Hz, 1H), 7.18 (m, 2H), 6.94 (d, J=5.6 Hz, 1H), 6.78 (d, J=5.6 Hz, 1H), 5.37 (t, J=6 Hz, 1H), 4.57 (d, J=6 Hz, 2H), 3.47 (s, 2H), 2.93 (d, J=12 Hz, 2H), 2.36 (d, J=11.6 Hz, 2H), 2.06 (t, J=12.8 Hz, 2H), 1.19 (d, J=10.4 Hz, 2H).

The following compounds are prepared essentially as described by the method of preparation 48

| Prep. No. | Chemical Name | ESI/MS (m/z) (M + H) |
|---|---|---|
| 49 | [3-Chloro-4-(spiro[indene-1,4'-piperidine]-1'-ylmethyl)phenyl]methanol | 339 |
| 50 | [2-Methoxy-4-(spiro[indene-1,4'-piperidine]-1'-ylmethyl)phenyl]methanol | 336 |
| 51 | [3-Fluoro-4-(spiro[indene-1,4'-piperidine]-1'-ylmethyl)phenyl]methanol | 324 |
| 52 | [4-(Spiro[indene-1,4'-piperidine]-1'-ylmethyl)-3-(trifluoromethyl)phenyl]methanol | 374 |
| 53 | [3-Chloro-4-[(1-methylspiro[indoline-3,4'-piperidine]-1'-yl)methyl]phenyl]methanol | 357 |
| 54 | [4-(Spiro[indane-1,4'-piperidine]-1'-ylmethyl)-3-(trifluoromethyl)phenyl]methanol | 376 |

Preparation 55

[4-(Spiro[indane-1,4'-piperidine]-1'-ylmethyl)phenyl]methanol

To a stirred solution of 2,3-dihydrospiro[indene-1,4'-piperidine] (0.4 g, 1.78 mmol) in DMF (12 mL) is added Cs$_2$CO$_3$ (1.4 g, 4.4 mmol) and [4-(bromomethyl)phenyl]methanol (0.36 g, 1.78 mmol) and the reaction mixture is stirred overnight at room temperature. The reaction mixture is poured into cold water and extracted with EtOAc (3×50 mL). The combined organic layer is washed with brine solution, dried over Na$_2$SO$_4$, and concentrated under vacuum. The crude material is purified by silica gel chromatography (gradient DCM/MeOH 8/2) to give the title compound (0.6 g, 98%). ESI/MS m/z 308.40 (M+H)$^+$.

Preparation 56

1'-[[4-(Bromomethyl)phenyl]methyl]spiro[indene-1,4'-piperidine]

To a 0° C. solution of [4-(spiro[indene-1,4'-piperidine]-1'-ylmethyl)phenyl]methanol (1.5 g, 4.91 mmol) in DCM (50 mL) is added phosphorus tribromide (0.667 mL, 6.8 mmol). The reaction mixture is stirred for 15 minutes at 0° C. The reaction mixture is diluted with water (100 mL) at 0° C. and extracted with DCM (2×200 mL). The combined extracts are washed with brine, dried over sodium sulfate, filtered, and concentrated to give the title compound as an off white solid (1.1 g, 61%). ESI/MS m/z 369 (M+H)$^+$.

The following compounds are prepared essentially as described by the method of preparation 56.

| Prep. No. | Chemical Name | ESI/MS (m/z) (M + H) |
|---|---|---|
| 57 | 1'-[[4-(Bromomethyl)-2-chloro-phenyl]methyl]spiro[indene-1,4'-piperidine] | 403 |
| 58 | 1'-[[4-(Bromomethyl)-3-methoxy-phenyl]methyl]spiro[indene-1,4'-piperidine] | 399 |
| 59 | 1'-[[4-(Bromomethyl)-2-fluoro-phenyl]methyl]spiro[indene-1,4'-piperidine] | 387 |
| 60 | 1'-[[4-(Bromomethyl)-2-(trifluoromethyl)phenyl]methyl]spiro[indene-1,4'-piperidine] | 438 |
| 61 | 1'-[[4-(Bromomethyl)phenyl]methyl]spiro[indane-1,4'-piperidine] | |

Preparation 62

[4-(Bromomethyl)-2-methoxy-phenyl]methoxy-tert-butyl-dimethyl-silane

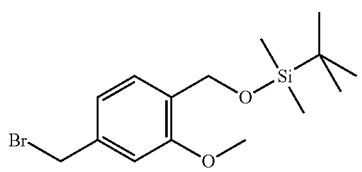 [SMILES: COc1cc(CBr)ccc1CO[Si](C)(C)C(C)(C)C]

To a solution of (4-bromomethyl-2-methoxy-phenyl)-methanol (1.1 g, 4.76 mmol) in dichloromethane (15 mL) is added imidazole (0.861 g, 5.71 mmol) and tert-butylchlorodimethylsilane (0.971 g, 12.98 mmol) at 0° C. The reaction mixture is allowed to warm to room temperature and stirred for one hour. The reaction mixture is quenched with water and concentrated. The residue is diluted with DCM, washed with water (15 mL) and brine (15 mL), dried over sodium sulfate, filtered, and concentrated to give the title compound (1.1 g, 66.9%). $^1$H NMR (400 MHz, CDCl$_3$) δ 7.43-7.41 (d, J=8 Hz, 1H), 7.00-6.98 (d, J=8 Hz, 1H), 6.94 (s, 1H), 4.73 (s, 2H), 4.50 (s, 2H), 3.83 (s, 3H), 0.95 (s, 9H), 0.10 (s, 6H).

The following compound is prepared essentially as described by the method of preparation 62

| Prep. No. | Chemical Name | ESI/MS (m/z) (M + H) |
|---|---|---|
| 63 | (4-Bromo-2-methyl-phenyl)methoxy-tert-butyl-diphenyl-silane | 440 |

Preparation 64

Ethyl 3-[4-[[4-[(tert-butyl(dimethyl)silyl)oxymethyl]-3-methoxy-phenyl]methoxy]-2-fluoro-phenyl]propanoate

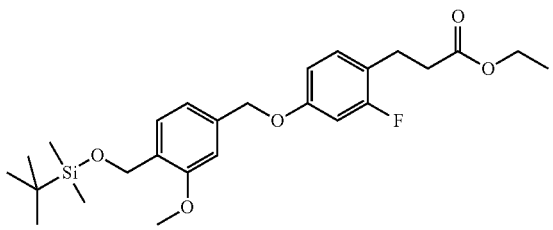 [SMILES: CCOC(=O)CCc1ccc(OCc2ccc(CO[Si](C)(C)C(C)(C)C)c(OC)c2)cc1F]

To a solution of 3-(2-fluoro-4-hydroxy-phenyl)-propionic acid ethyl ester (0.54 g, 3.188 mmol) in ACN (20 mL) is added potassium carbonate (1.32 g, 9.56 mmol) and 4-bromomethyl-2-methoxy-benzyloxy)-tert-butyl-dimethyl-silane (1.1 g, 3.188 mmol) at room temperature and the reaction mixture is stirred for 16 hours at 25° C. The reaction mixture is concentrated, diluted with water, and extracted with EtOAc (2×50 mL). The combined extracts are washed with water (15 mL) and saturated brine (15 mL), dried over Na$_2$SO$_4$, filtered, and concentrated to give the title compound as a colorless gel (1 g, 66.66%). $^1$H NMR (400 MHz, CDCl$_3$) δ 7.47-7.45 (d, J=8 Hz, 1H), 7.11-7.07 (t, J=8 Hz, 1H), 7.00-6.98 (d, J=8 Hz, 1H), 6.87 (s, 1H), 6.69-6.65 (t, J=5.2 Hz, 2H), 5.00 (s, 2H), 4.74 (s, 2H), 4.14-4.09 (q, 2H), 3.83 (s, 3H), 2.91-2.88 (t, 3H), 2.59-2.26 (t, 2H), 1.25-1.22 (t, 2H), 0.95 (s, 9H), 0.10 (s, 6H).

The following compounds are prepared essentially as described by the method of preparation 64.

| Prep. No. | Chemical Name | ESI/MS (m/z) (M + H) |
|---|---|---|
| 65 | Ethyl (3S)-3-[4-[[4-[(tert-butyl(dimethyl)silyl)oxymethyl]-3-methoxy-phenyl]methoxy]phenyl]hex-4-ynoate | a |
| 66 | Ethyl 3-[4-[[4-[(tert-butyl(diphenyl)silyl)oxymethyl]-3-methyl-phenyl]methoxy]-2-fluoro-phenyl]propanoate | 496 | a. $^1$H NMR (400 MHz, CDCl$_3$) δ 7.46-7.44 (d, J = 8 Hz, 1H), 7.28-7.25 (d, J = 12 Hz, 2H), 7.00-6.98 (d, J = 8 Hz, 1H), 6.92-6.88 (t, J = 12 Hz, 3H), 5.01 (s, 2H), 4.74 (s, 2H), 4.12-4.05 (m, 3H), 3.81 (s, 3H), 2.71-2.64 (m, 2H), 1.81 (s, 3H), 1.25-1.21 (t, J = 8 Hz, 3H), 0.95 (s, 9H).

Preparation 67

Ethyl 3-[2-fluoro-4-[[4-(hydroxymethyl)-3-methoxy-phenyl]methoxy]phenyl]propanoate

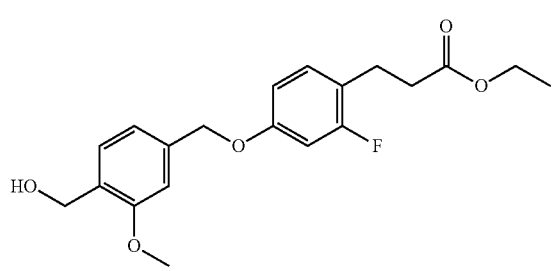 [SMILES: CCOC(=O)CCc1ccc(OCc2ccc(CO)c(OC)c2)cc1F]

To a solution of 3-{4-[4-(tert-butyl-dimethyl-silanyloxymethyl)-3-methoxy-benzyloxy]-2-fluoro-phenyl}-propionic acid ethyl ester (1 g, 2.1 mmol) in THF (15 mL) is added tetra-n-butylammoniumfluoride (1 M in THF, 3.15 mL, 3.15 mmol) at 0° C. and the reaction mixture is stirred for 2 hour at 25° C. The reaction mixture is quenched with water and concentrated. The residue is diluted with EtOAc, washed with water (15 mL) and brine (15 mL), dried over sodium sulfate, filtered, and concentrated to give the title compound (1.0 g, crude). The crude product is used without further purification.

The following compounds are prepared essentially as described by the method of preparation 67.

| Prep. No. | Chemical Name | ESI/MS (m/z) (M + H) |
|---|---|---|
| 68 | Ethyl (3S)-3-[4-[[4-(hydroxymethyl)-3-methoxy-phenyl]methoxy]phenyl]hex-4-ynoate | |
| 69 | Ethyl 3-[2-fluoro-4-[[4-(hydroxymethyl)-3-methyl-phenyl]methoxy]phenyl]propanoate | 319 |
| 70 | Ethyl (3S)-3-[4-[[4-(hydroxymethyl)-3-methyl-phenyl]methoxy]phenyl]hex-4-ynoate | a | a. $^1$H NMR (d6-DMSO, 400 MHz) δ 7.37-7.35 (d, J = 8 Hz, 1H), 7.30-7.29 (m, 2H), 7.259-7.24 (m, 2H), 6.92-6.89 (dd, J = 12 Hz, 2H), 5.00 (s, 2H), 4.70 (s, 2H), 4.13-4.11 (q, J = 8 Hz, 2H), 2.72-2.65 (m, 2H), 2.36 (s, 1H), 2.18 (s, 2H), 1.82 (s, 3H), 1.27-1.23 (t, J = 8 Hz, 3H), 1.087 (s, 9H).

Preparation 71

Ethyl 3-[4-[[4-(bromomethyl)-3-methoxy-phenyl]methoxy]-2-fluoro-phenyl]propanoate

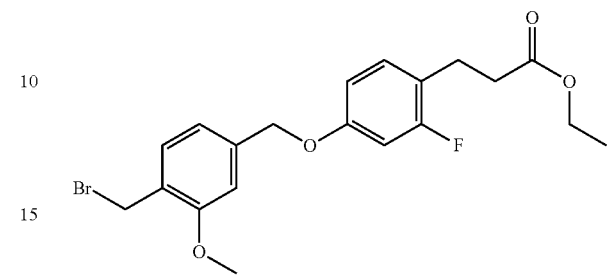

To a solution of 3-[2-fluoro-4-(4-hydroxymethyl-3-methoxy-benzyloxy)-phenyl]-propionic acid ethyl ester (1.0 g, 2.76 mmol) in dichloromethane (25 mL) is added phosphorus tribromide (0.4 mL, 4.41 mmol) at 0° C. and the reaction mixture is stirred for 15 min at 0° C. The mixture is cooled to 0° C., diluted with water, and extracted with dichloromethane (2×100 mL). The combined extracts are washed with saturated brine, dried over Na$_2$SO$_4$, filtered, and concentrated to give the title compound (1.1 g, crude). $^1$H NMR (DMSO, 400 MHz) δ 7.34-7.32 (d, J=8 Hz, 1H), 7.12-7.08 (t, J=8 Hz, 1H), 6.96-6.94 (d, J=8 Hz, 2H), 6.67-6.64 (d, J=12 Hz, 2H), 4.98 (s, 2H), 4.55 (s, 2H), 4.12-4.09 (q, 2H), 2.90-2.88 (t, 2H), 2.60-2.56 (t, J=8 Hz, 2H), 1.25-1.22 (t, J=8 Hz, 3H).

The following compounds are prepared essentially as described by the method of preparation 71.

| Prep. No. | Chemical Name | ESI/MS (m/z) (M + H) |
|---|---|---|
| 72 | Ethyl (3S)-3-[4-[[4-(bromomethyl)-3-methoxy-phenyl]methoxy]phenyl]hex-4-ynoate | |
| 73 | Ethyl 3-[4-[[4-(bromomethyl)-3-methyl-phenyl]methoxy]-2-fluoro-phenyl]propanoate | 410 |
| 74 | Ethyl (3S)-3-[4-[[4-(bromomethyl)-3-methyl-phenyl]methoxy]phenyl]hex-4-ynoate | 430 |

Preparation 75

4-[(tert-Butyl(diphenyl)silyl)oxymethyl]-3-methyl-benzaldehyde

To a stirred solution of (4-bromomethyl-2-methyl-benzyloxy)-tert-butyl-diphenyl-silane (3 g, 6.83 mmol) in tetrahydrofuran is added sec-butyl lithium at −78° C. under nitrogen atmosphere. The reaction mixture is warmed to 0° C. and stirred for 30 min. The reaction mixture is cooled to −78° C., N-formyl piperidine (1.13 mL, 10.24 mmol) is added, and the reaction mixture is stirred for 3 hours at room temperature. The reaction mixture is quenched with water at 0° C. and extracted with EtOAc (50 mL×3). The combined organic layer is washed with brine solution, dried over magnesium sulphate, and concentrated under vacuum to give the title compound (3 g, 46%). ESI/MS m/z 389.1 (M+H)$^+$.

Preparation 76

[4-[(tert-Butyl(diphenyl)silyl)oxymethyl]-3-methylphenyl]methanol

To a stirred solution of 4-(tert-butyl-diphenyl-silanyloxymethyl)-3-methyl-benzaldehyde (0.1 g, 0.257 mmol) in anhydrous DCM is slowly added diisobutylaluminum hydride (1.0 M in hexane, 0.3 mL, 0.3 mmol) to the mixture at −78° C. After the addition is complete, the reaction mixture is warmed to room temperature and stirred for 2 h. An aqueous solution of 2 N sodium potassium tartrate tetrahydrate (10 mL) is added to the reaction mixture and the mixture is agitated for 30 minutes. The reaction product is extracted with DCM (20 mL), dried over magnesium sulfate, and concentrated to dryness to give the title compound (0.3 g, 30%). ESI/MS m/z 391.1 (M+H)+.

Preparation 77

[4-(Bromomethyl)-2-methyl-phenyl]methoxy-tert-butyl-diphenyl-silane

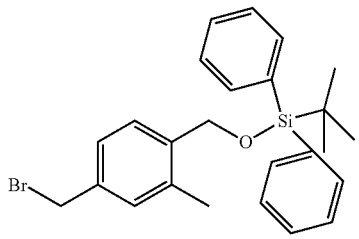 [SMILES: Cc1cc(CBr)ccc1CO[Si](c1ccccc1)(c1ccccc1)C(C)(C)C]

To a stirred solution of [4-[(tert-butyl(diphenyl)silyl)oxymethyl]-3-methyl-phenyl]methanol (0.3 g, 0.76 mmol) in DCM (30 mL) is added phosphorus tribromide (0.072 mL, 0.76 mmol) at 0° C. and the reaction mixture is stirred for 1 hour. The reaction mixture is diluted with dichloromethane (50 mL), washed with aqueous sodium bicarbonate solution, dried over magnesium sulphate, and concentrated under vacuum to give the title compound as a light yellow liquid (0.3 g, crude). ESI/MS m/z 438.1 (M+H)+.

Preparation 78

Ethyl (3S)-3-[4-[[4-[(tert-butyl(diphenyl)silyl)oxymethyl]-3-methyl-phenyl]methoxy]phenyl]hex-4-ynoate

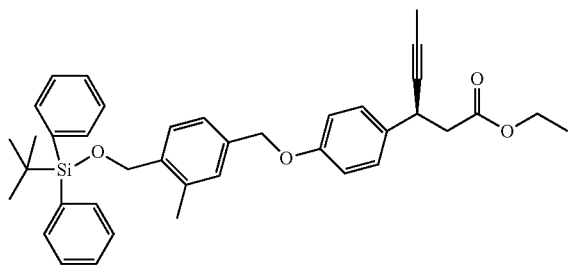 [SMILES: CC#C[C@@H](CC(=O)OCC)c1ccc(OCc2ccc(CO[Si](c3ccccc3)(c3ccccc3)C(C)(C)C)c(C)c2)cc1]

To a solution of 1,1'-(azodicarbonyl)dipiperidine (0.770 g, 3.075 mmol) in THF is added tributylphosphine (50% in EtOAc, 7.17 mL, 3.58 mmol) at 0-5° C. The reaction mixture is stirred for 30 minutes at room temperature. [4-(tert-butyl-diphenyl-silanyloxymethyl)-3-methyl-phenyl]-methanol (0.8 g, 2.05 mmol) is added at 0° C. The reaction mixture is stirred for 30 min and 3-(4-hydroxy-phenyl)-hex-4-ynoic acid ethyl ester (0.523 g, 2.25 mmol) is added. The mixture is warmed to room temperature and stirred overnight. Hexane (75 mL) is added to the reaction mixture and the precipitate formed is filtered off. The filtrate is concentrated under reduced pressure. The residue is purified by silica gel column chromatography (gradient of 10 to 30% EtOAc:hexane) to give the title compound (1.3 g, 83%). $^1$H (d$_6$-DMSO, 400 MHz) δ 7.70-7.68 (d, J=8 Hz, 3H), 7.53-7.51 (d, J=8 Hz, 1H), 7.42-7.41 (m, 5H), 7.39-7.35 (m, 4H), 7.29-7.25 (d, J=16 Hz, 2H), 6.93-6.91 (d, J=8 Hz, 2H), 5.00 (s, 2H), 4.72 (s, 2H), 4.13-4.11 (q, J=8 Hz, 2H), 2.72-2.65 (m, 2H), 2.36 (s, 1H), 2.18 (s, 2H), 1.82 (s, 3H), 1.27-1.23 (t, J=8 Hz, 3H), 1.087 (s, 9H).

Preparation 79

Ethyl (3S)-3-[4-[[4-(spiro[indene-1,4'-piperidine]-1'-ylmethyl)phenyl]methoxy]phenyl]hex-4-ynoate

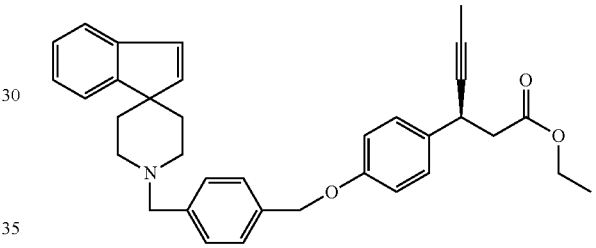

To a solution of ethyl(3S)-3-(4-hydroxyphenyl)hex-4-ynate (0.350 g, 1.5 mmol) in acetonitrile (25 mL) is added potassium carbonate (0.621 g, 4.5 mmol) and 1'-[4-(bromomethyl)benzyl]spiro[indene-1,4'-piperidine] (0.77 g, 2.1 mmol). The reaction mixture is heated for 16 hours at 90° C. The mixture is concentrated, diluted with water, and extracted with EtOAc (2×200 mL). The combined extracts are washed with water (50 mL), brine (50 mL), dried over sodium sulfate, filtered, and concentrated to dryness to give the title compound (0.3 g, 38%). ESI/MS m/z 520 (M+H)+.

The following compounds are prepared essentially as described by the method of preparation 79.

| Prep. No. | Chemical Name | ESI/MS (m/z) (M + H) |
|---|---|---|
| 80 | Ethyl 3-[2-fluoro-4-[[4-(spiro[indene-1,4'-piperidine]-1'-ylmethyl)phenyl]methoxy]phenyl]propanoate | 500 |
| 81 | Ethyl 3-[4-[[3-chloro-4-(spiro[indene-1,4'-piperidine]-1'-ylmethyl)phenyl]methoxy]-2-fluoro-phenyl]propanoate | 534 |
| 82 | Ethyl 3-[2-fluoro-4-[[2-methoxy-4-(spiro[indene-1,4'-piperidine]-1'-ylmethyl)phenyl]methoxy]phenyl]propanoate | 530 |

-continued

| Prep. No. | Chemical Name | ESI/MS (m/z) (M + H) |
|---|---|---|
| 83 | Ethyl 3-[2-fluoro-4-[[3-fluoro-4-(spiro[indene-1,4'-piperidine]-1'-ylmethyl)phenyl]methoxy]phenyl]propanoate | 518 |
| 84 | Ethyl 3-[2-fluoro-4-[[4-(spiro[indene-1,4'-piperidine]-1'-ylmethyl)-3-(trifluoromethyl)phenyl]methoxy]phenyl]propanoate | 568 |
| 85 | Ethyl (3S)-3-[4-[[3-chloro-4-(spiro[indene-1,4'-piperidine]-1'-ylmethyl)phenyl]methoxy]phenyl]hex-4-ynoate | 554 |

Preparation 86

Ethyl 3-[2-fluoro-4-[[4-(spiro[indane-1,4'-piperidine]-1'-ylmethyl)phenyl]methoxy]phenyl]propanoate A mixture of 1'-[4-(bromomethyl)benzyl]-2,3-dihydrospiro[indene-1,4'-piperidine] (0.35 g, 0.94 mmol), ethyl 3-(2-fluoro-4-hydroxyphenyl)propanoate (0.2 g, 0.94 mmol) and K₂CO₃ (0.32 g, 2.3 mmol) in DMF (15 mL) is stirred overnight at room temperature. The reaction mixture is diluted with cold water and extracted with DCM (3×50 mL). The combined organic layer is washed with brine solution, dried over Na₂SO₄, and concentrated under vacuum. The crude material is purified by silica gel chromatography (gradient DCM/MeOH 8/2) to give the title compound as an off-white solid (0.22 g, crude). ESI/MS 502 (M+H)⁺.

Preparation 87

Methyl 3-[2-fluoro-4-[[4-(spiro[indene-1,4'-piperidine]-1'-ylmethyl)phenyl]methoxy]phenyl]hex-4-ynoate, Isomer 1

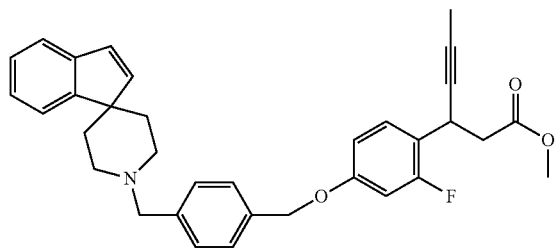 [SMILES: CC#CC(CC(=O)OC)c1ccc(OCc2ccc(CN3CCC4(C=Cc5ccccc54)CC3)cc2)cc1F]

To a solution of ADDP (0.302 g, 1.2 mmol) in THF (2 mL) is added tributylphosphine (0.291 g, 1.44 mmol) at 0° C. and stirred at 0° C. for 15 min. A solution of [4-(1'H-spiro[indene-1,4'-piperidin]-1'-ylmethyl)phenyl]methanol (0.219 g, 0.9 mmol) in THF (2 mL) is added and the reaction mixture is stirred for 15 min at 0° C. A solution of 3-(2-fluoro-4-hydroxy-phenyl)-hex-4-ynoic acid methyl ester (isomer-1, 0.200 g, 0.8 mmol) in THF (2 mL) is added at 0° C. and the reaction mixture is stirred for 16 hours at room temperature. The reaction mixture is diluted with hexane, filtered over diatomaceous earth and the filtrate is evaporated. The crude material is purified by silica gel chromatography using an ethyl acetate gradient (6:4) to give title compound as a liquid (0.220 g, 42%). ESI/MS m/z 524 (M+H)⁺.

The following compounds are prepared essentially as described by the method of preparation 87.

| Prep. No. | Chemical Name | ESI/MS (m/z) (M + H) |
|---|---|---|
| 88 | Ethyl 3-[2-chloro-4-[[4-(spiro[indene-1,4'-piperidine]-1'-ylmethyl)phenyl]methoxy]phenyl]propanoate | 517 |
| 89 | Ethyl 3-[4-[[4-(spiro[indene-1,4'-piperidine]-1'-ylmethyl)phenyl]methoxy]phenyl]hex-4-ynoate | 520 |
| 90 | Ethyl (3S)-3-[4-[[3-chloro-4-[(1-methylspiro[indoline-3,4'-piperidine]-1'-yl)methyl]phenyl]methoxy]phenyl]hex-4-ynoate | 571 |
| 91 | Ethyl (3S)-3-[4-[[3-fluoro-4-(spiro[indene-1,4'-piperidine]-1'-ylmethyl)phenyl]methoxy]phenyl]hex-4-ynoate | 538 |
| 92 | Ethyl (3S)-3-[4-[[4-(spiro[indane-1,4'-piperidine]-1'-ylmethyl)-3-(trifluoromethyl)phenyl]methoxy]phenyl]hex-4-ynoate | 490 |
| 93 | Ethyl 3-[2-fluoro-4-[[4-(spiro[indane-1,4'-piperidine]-1'-ylmethyl)-3-(trifluoromethyl)phenyl]methoxy]phenyl]propanoate | 570 |

Preparation 94

Ethyl (3S)-3-[4-[[4-[(1-methylspiro[indoline-3,4'-piperidine]-1'-yl)methyl]phenyl]methoxy]phenyl]hex-4-ynoate

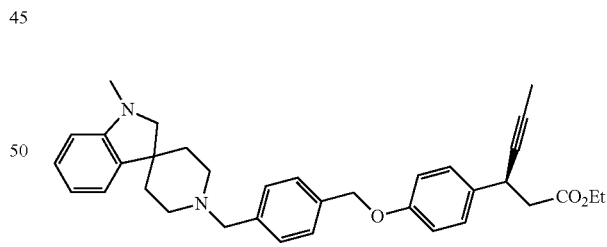

A mixture of 1-methylspiro[indoline-3,4'-piperidine] (0.0486 g, 0.204 mmol), ethyl (3S)-3-(4-{[4-(bromomethyl)benzyl]oxy}phenyl)hex-4-ynoate (0.100 g, 0.24 mmol), and Cs₂CO₃ (0.156 g, 0.48 mmol) in DMF (5 mL) is stirred at room temperature for 16 hours. The reaction mixture is diluted with water (30 mL) and extracted with EtOAc (3×25 mL). The combined organic layer is washed with water (3×25 mL) and saturated brine solution (25 mL), dried with a drying agent, filtered, and evaporated to dryness to give a liquid. The crude product is purified by silica gel chromatography (gradient EtOAc/hexane 30%) to give the title compound as a colourless liquid (0.095 g, 73.3%). ESI/MS m/z 537 (M+H)⁺.

The following compounds are prepared essentially as described by the method of preparation 94.

| Prep. No. | Chemical Name | ESI/MS (m/z) (M + H) |
|---|---|---|
| 95 | Ethyl 3-[2-fluoro-4-[[4-[(1-methylspiro[indoline-3,4'-piperidine]-1'-yl)methyl]phenyl]methoxy]phenyl]propanoate | 517 |
| 96 | tert-Butyl 1'-[[4-[[4-(3-ethoxy-3-oxo-propyl)-3-fluoro-phenoxy]methyl]phenyl]methyl]spiro[indoline-3,4'-piperidine]-1-carboxylate | 603 |
| 97 | Ethyl 3-[4-[[4-[(7-chloro-1-methyl-spiro[indoline-3,4'-piperidine]-1'-yl)methyl]phenyl]methoxy]-2-fluoro-phenyl]propanoate | 551 |
| 98 | Ethyl (3S)-3-[4-[[4-[(7-chloro-1-methyl-spiro[indoline-3,4'-piperidine]-1'-yl)methyl]phenyl]methoxy]phenyl]hex-4-ynoate | 571 |
| 99 | Ethyl 3-[2-fluoro-4-[[4-[(5-fluoro-1-methyl-spiro[indoline-3,4'-piperidine]-1'-yl)methyl]phenyl]methoxy]phenyl]propanoate | 535 |
| 100 | Ethyl 3-[2-fluoro-4-[[4-[(5-methoxy-1-methyl-spiro[indoline-3,4'-piperidine]-1'-yl)methyl]phenyl]methoxy]phenyl]propanoate | 547 |
| 101 | Ethyl (3S)-3-[4-[[4-[(5-methoxy-1-methyl-spiro[indoline-3,4'-piperidine]-1'-yl)methyl]phenyl]methoxy]phenyl]hex-4-ynoate | 567 |
| 102 | Ethyl (3S)-3-[4-[[4-[(1,5-dimethylspiro[indoline-3,4'-piperidine]-1'-yl)methyl]phenyl]methoxy]phenyl]hex-4-ynoate | 551 |
| 103 | Ethyl 3-[2-fluoro-4-[[4-[[1-methyl-5-(trifluoromethyl)spiro[indoline-3,4'-piperidine]-1'-yl]methyl]phenyl]methoxy]phenyl]propanoate | 585 |
| 104 | Ethyl (3S)-3-[4-[[4-[[1-methyl-5-(trifluoromethyl)spiro[indoline-3,4'-piperidine]-1'-yl]methyl]phenyl]methoxy]phenyl]hex-4-ynoate | 605 |
| 105 | Ethyl (3S)-3-[4-[[4-[(1-isopropylspiro[indoline-3,4'-piperidine]-1'-yl)methyl]phenyl]methoxy]phenyl]hex-4-ynoate | 566 |
| 106 | Ethyl 3-[2-fluoro-4-[[4-[(1-isopropylspiro[indoline-3,4'-piperidine]-1'-yl)methyl]phenyl]methoxy]phenyl]propanoate | 546 |
| 107 | Ethyl 3-[2-fluoro-4-[[4-[(1-phenylspiro[indoline-3,4'-piperidine]-1'-yl)methyl]phenyl]methoxy]phenyl]propanoate | 579 |
| 108 | Ethyl (3S)-3-[4-[[4-[(1-phenylspiro[indoline-3,4'-piperidine]-1'-yl)methyl]phenyl]methoxy]phenyl]hex-4-ynoate | 599 |
| 109 | Ethyl 3-[2-fluoro-4-[[4-[(3-oxospiro[indane-1,4'-piperidine]-1'-yl)methyl]phenyl]methoxy]phenyl]propanoat | 516 |

Preparation 110

Ethyl (3S)-3-[4-[[4-(spiro[indane-1,4'-piperidine]-1'-ylmethyl)phenyl]methoxy]phenyl]hex-4-ynoate

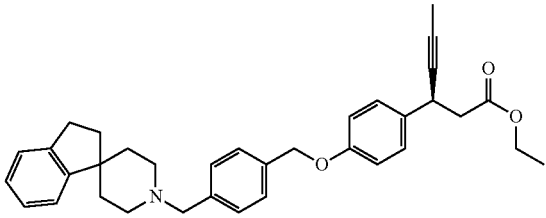 [SMILES: CC#C[C@@H](CC(=O)OCC)c1ccc(OCc2ccc(CN3CCC4(CCc5ccccc54)CC3)cc2)cc1]

To a solution of 2,3-dihydrospiro[indene-1,4'-piperidine] (0.37 g, 1.68 mmol) in acetonitrile (20.0 mL), is added Cs$_2$CO$_3$ (1.37 g, 4.21 mmol at room temperature, followed by the addition of 3-[4-(4-bromomethyl-benzyloxy)-phenyl]-hex-4-ynoic acid ethyl ester (0.70 g, 1.68 mmol). The reaction mixture is stirred overnight at room temperature. The reaction mixture is filtered through diatomaceous earth and the filtrate is evaporated. The crude product is purified by silica gel column chromatography (gradient 3% methanol in DCM) to give the title compound as colorless gel, (0.82 g, 93.7%). ESI/MS 522.2 (M+H)$^+$.

Preparation 111

Ethyl 3-[2-fluoro-4-[[3-methoxy-4-(spiro[indene-1,4'-piperidine]-1'-ylmethyl)phenyl]methoxy]phenyl]propanoate

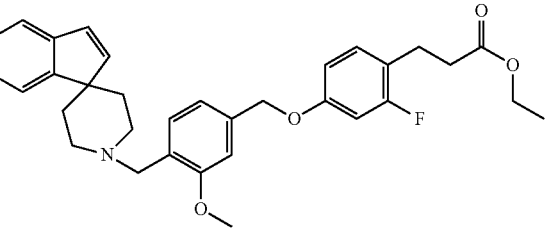

To a solution of spiro[indene-1,4'-piperidine] (0.515 g, 2.58 mmol) in EtOH (15 mL) is added N,N-diisopropylethylamine (1.4 mL, 2.589 mmol) and 3-[4-(4-bromomethyl-2-trifluoromethyl-benzyloxy)-2-fluoro-phenyl]-propionic acid ethyl ester (1.1 g, 2.58 mmol) at room temperature and the reaction mixture is stirred for 16 hours at 80° C. The mixture is concentrated, diluted with water, and extracted with EtOAc (2×50 mL). The combined extracts are washed with water (20 mL) and saturated brine (20 mL), dried over Na$_2$SO$_4$, filtered, and concentrated. The crude material is purified by silica gel column chromatography to give the title compound as a colorless gel (0.650 g, 47.7%). $^1$H NMR (400 MHz, CDCl$_3$) δ 7.42-7.35 (m, 2H), 7.31-7.29 (d, J=8 Hz, 1H), 7.20-7.01 (m, 3H), 7.05 (s, 1H), 7.01-6.99 (d, J=8 Hz, 1H), 6.64-6.93 (d, J=4 Hz, 1H), 6.86-6.83 (d, J=12 Hz, 1H) 6.77 (s, 1H), 5.05 (s, 2H), 4.03-3.98 (m, 2H), 3.79 (s, 3H), 3.57 (s, 2H), 2.89-2.86 (d, J=12 Hz, 2H), 2.79-2.76 (t, J=8 Hz, 2H), 2.55-2.53 (d, J=8 Hz, 2H), 2.41-2.35 (t, J=12 Hz, 2H), 2.10-2.05 (t, J=8 Hz, 2H), 1.22-1.17 (t, J=8 Hz, 3H).

The following compounds are prepared essentially as described by the method of preparation 111.

| Prep. No. | Chemical Name | ESI/MS (m/z) (M + H) |
|---|---|---|
| 112 | Ethyl (3S)-3-[4-[[3-methoxy-4-(spiro[indene-1,4'-piperidine]-1'-ylmethyl)phenyl]methoxy]phenyl]hex-4-ynoate | 550 |
| 113 | Ethyl 3-[2-fluoro-4-[[3-methoxy-4-[(1-methylspiro[indoline-3,4'-piperidine]-1'-yl)methyl]phenyl]methoxy]phenyl]propanoate | 549 |
| 114 | Ethyl (3S)-3-[4-[[3-methoxy-4-[(1-methylspiro[indoline-3,4'-piperidine]-1'-yl)methyl]phenyl]methoxy]phenyl]hex-4-ynoate | 567 |
| 115 | Ethyl 3-[2-fluoro-4-[[3-methyl-4-(spiro[indene-1,4'-piperidine]-1'-ylmethyl)phenyl]methoxy]phenyl]propanoate | 514 |
| 116 | Ethyl (3S)-3-[4-[[3-methyl-4-(spiro[indene-1,4'-piperidine]-1'-ylmethyl)phenyl]methoxy]phenyl]hex-4-ynoate | 534 |

Preparation 117

3-[4-[[4-[(1-tert-Butoxycarbonylspiro[indoline-3,4'-piperidine]-1'-yl)methyl]phenyl]methoxy]-2-fluoro-phenyl]propanoic acid

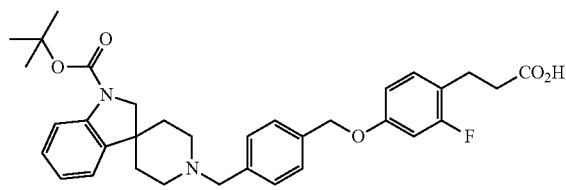 [SMILES: CC(C)(C)OC(=O)N1CC2(CCN(Cc3ccc(COc4ccc(CCC(=O)O)c(F)c4)cc3)CC2)c2ccccc21]

A mixture of tert-butyl 1'-[[4-[[4-(3-ethoxy-3-oxo-propyl)-3-fluoro-phenoxy]methyl]phenyl]methyl]spiro[indoline-3,4'-piperidine]-1-carboxylate (0.32 g, 0.53 mmol) and KOH (0.148 g, 2.65 mmol) in ethanol:water (3:1, 4 mL) is stirred at room temperature for 16 hours. The reaction mixture is evaporated to dryness. The residue is re-dissolved in water (8 mL), cooled to 0° C., acidified with 1.5 N HCl to pH~6, and extracted with EtOAc (3×15 mL). The combined organic layer is washed with water (15 mL) and saturated brine solution (15 mL), dried with a drying agent, filtered, and evaporated to dryness to give the title compound as an off-white solid (0.22 g, 72.1%). ESI/MS m/z 575.6 (M+H)$^+$.

Preparation 118

Methyl 3-[2-fluoro-4-[[4-(spiro[indoline-3,4'-piperidine]-1'-ylmethyl)phenyl]methoxy]phenyl]propanoate hydrochloride

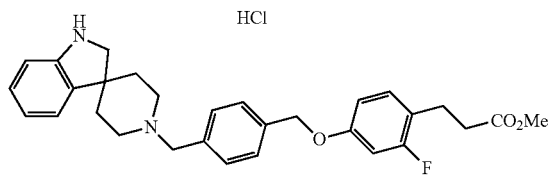 [SMILES: Cl ; COC(=O)CCc1ccc(OCc2ccc(CN3CCC4(CC3)CNc3ccccc34)cc2)cc1F]

To a solution of tert-butyl spiro[indole-3,4'-piperidine]-1 (2H)-carboxylate-3-{2-fluoro-4-[(4-methylbenzyl)oxy]phenyl}propanoic acid (0.12 g, 0.208 mmol) in methanol (5 mL), is added HCl in methanol (4 M, 5 mL) at 0° C. The reaction mixture is allowed to warm to room temperature and stirred for 1 hour. The reaction mixture is evaporated to dryness to give the title compound as a pale yellow solid (0.07 g, 64%). ESI/MS m/z 489.6 (M+H)$^+$.

Example 1

(3S)-3-(4-{[4-(1'H-Spiro[indene-1,4'-piperidin]-1'-ylmethyl)benzyl]oxy}phenyl)hex-4-ynoic acid

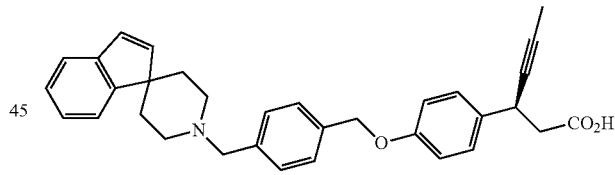

To a stirred solution of ethyl (3S)-3-[4-[[4-spiro[indene-1,4'-piperidine]-1'-ylmethyl)phenyl]methoxy]phenyl]hex-4-ynoate (0.3 g, 0.58 mmol) in ethanol (12 mL) is added, 5.0 M sodium hydroxide (0.231 mL, 1.156 mmol). The reaction mixture is irradiated with microwave radiation at 90° C. for 5 minutes. The reaction mixture is concentrated to dryness, diluted with water, and acidified with 2 N HCl to pH ~4 to give a precipitate which is collected by filtration. The solid is washed with water (5 mL) and hexane (10 mL) and dried to give the title compound as a white solid (0.210 g, 73%). ESI/MS m/z 492.1 (M+H)$^+$.

This material could be purified directly or combined with other lots for silica gel chromatography purification using 10% MeOH/DCM to give the title compound as a white solid (0.31 g). ESI/MS m/z 492.1 (M+H)$^+$.

The following compounds are prepared essentially by the method of Example 1.

| Ex No. | Chemical Name | Structure | ESI/MS (m/z) (M + H) |
|---|---|---|---|
| 2 | 3-(2-Fluoro-4-{[4-(1'H-spiro[indene-1,4'-piperidin]-1'-ylmethyl)benzyl]oxy}phenyl)propanoic acid | 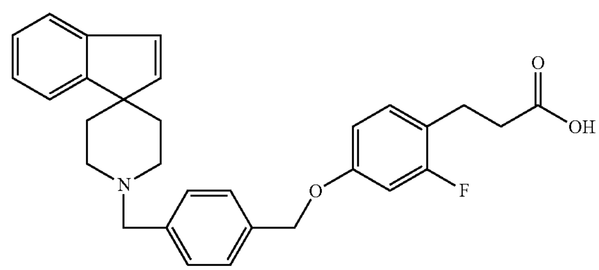 [SMILES: O=C(O)CCc1ccc(OCc2ccc(CN3CCC4(C=Cc5ccccc54)CC3)cc2)cc1F] | 472 |
| 3 | 3-[2-Fluoro-4-[[4-(spiro[indene-1,4'-piperidine]-1'-ylmethyl)phenyl]methoxy]phenyl]hex-4-ynoic acid, Isomer 1 | Isomer 1 | 510 |
| 4 | 3-(2-Chloro-4-{[4-(1'H-spiro[indene-1,4'-piperidin]-1'-ylmethyl)benzyl]oxy}phenyl)propanoic acid | 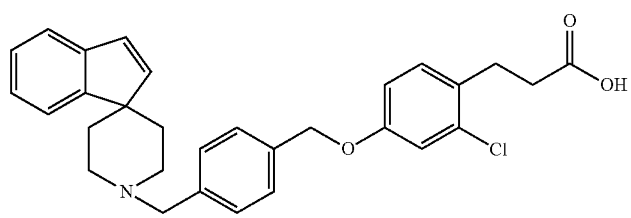 [SMILES: O=C(O)CCc1ccc(OCc2ccc(CN3CCC4(C=Cc5ccccc54)CC3)cc2)cc1Cl] | 488 |
| 5 | 3-(4-{[4-(1'H-Spiro[indene-1,4'-piperidin]-1'-ylmethyl)benzyl]oxy}phenyl)hex-4-ynoic acid | 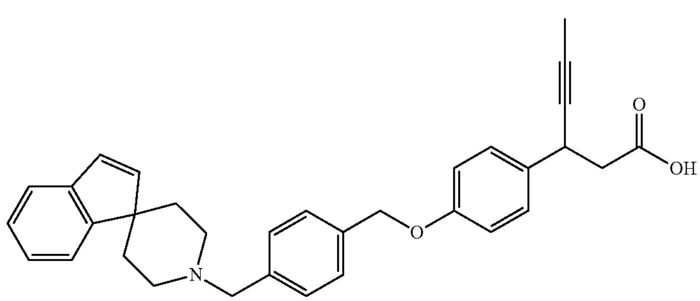 [SMILES: CC#CC(CC(=O)O)c1ccc(OCc2ccc(CN3CCC4(C=Cc5ccccc54)CC3)cc2)cc1] | 492 |
| 6 | (3S)-3-{4-[(4-{[1-(1-Methylethyl)-1,2-dihydro-1'H-spiro[indole-3,4'-piperidin]-1'-yl]methyl}benzyl)oxy]phenyl}hex-4-ynoic acid | 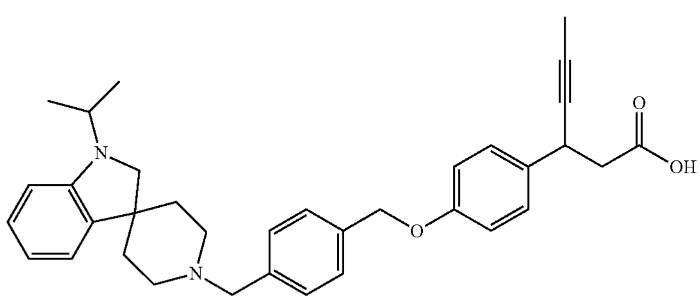 [SMILES: CC#CC(CC(=O)O)c1ccc(OCc2ccc(CN3CCC4(CC3)CN(C(C)C)c3ccccc34)cc2)cc1] | 536 |

| Ex No. | Chemical Name | Structure | ESI/MS (m/z) (M + H) |
|---|---|---|---|
| 7 | 3-{2-Fluoro-4-[(4-{[1-(1-methylethyl)-1,2-dihydro-1'H-spiro[indole-3,4'-piperidin]-1'-yl]methyl}benzyl)oxy]phenyl}propanoic acid | 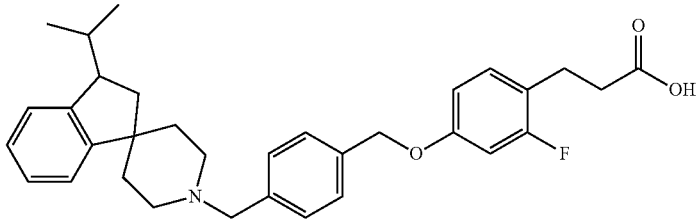 [SMILES: CC(C)C1CC2(CCN(Cc3ccc(COc4ccc(CCC(=O)O)c(F)c4)cc3)CC2)c2ccccc21] | 517 |
| 8 | 3-[2-Fluoro-4-({4-[(1-phenyl-1,2-dihydro-1'H-spiro[indole-3,4'-piperidin]-1'-yl)methyl]benzyl}oxy)phenyl]propanoic acid | 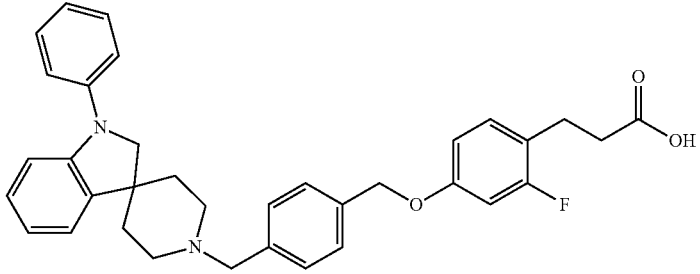 [SMILES: O=C(O)CCc1ccc(OCc2ccc(CN3CCC4(CC3)CN(c3ccccc3)c3ccccc34)cc2)cc1F] | 551 |
| 9 | 3-(4-{[3-Chloro-4-(1'H-spiro[indene-1,4'-piperidin]-1'-ylmethyl)benzyl]oxy}-2-fluorophenyl)propanoic acid | 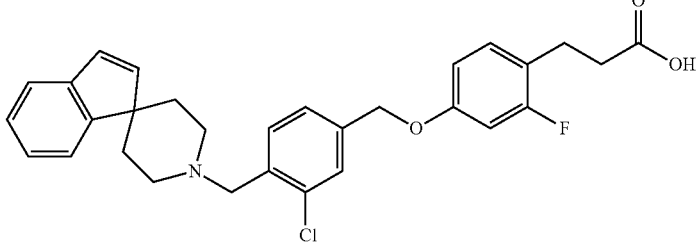 | 507 |
| 10 | (3S)-3-(4-{[3-Chloro-4-(1'H-spiro[indene-1,4'-piperidin]-1'-ylmethyl)benzyl]oxy}phenyl)hex-4-ynoic acid | 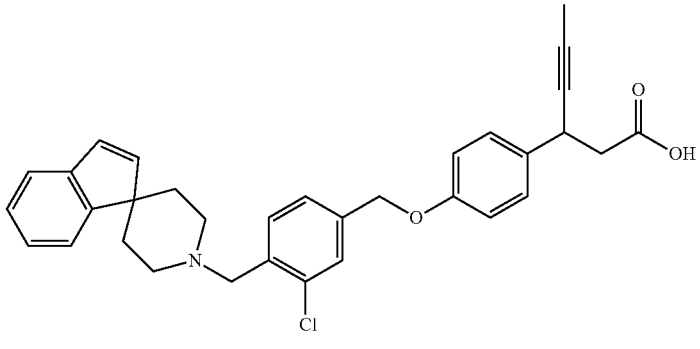 [SMILES: CC#CC(CC(=O)O)c1ccc(OCc2ccc(CN3CCC4(C=Cc5ccccc54)CC3)c(Cl)c2)cc1] | 527 |
| 11 | (3S)-3-[4-({3-Chloro-4-[(1-methyl-1,2-dihydro-1'H-spiro[indole-3,4'-piperidin]-1'-yl)methyl]benzyl}oxy)phenyl]hex-4-ynoic acid | 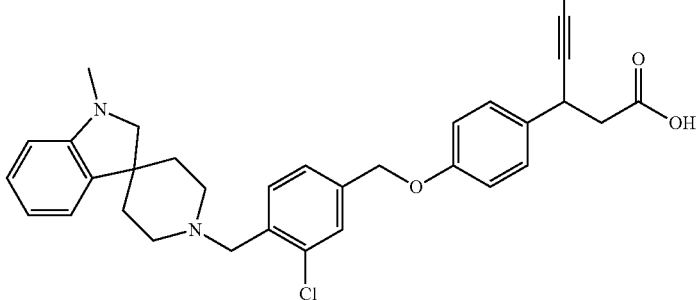 | 543 |

-continued

| Ex No. | Chemical Name | Structure | ESI/MS (m/z) (M + H) |
|---|---|---|---|
| 12 | 3-(2-Fluoro-4-{[2-methoxy-4-(1'H-spiro[indene-1,4'-piperidin]-1'-ylmethyl)benzyl]oxy}phenyl)propanoic acid | 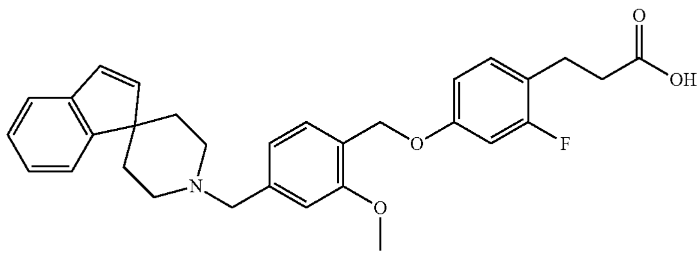 [SMILES: COc1cc(CN2CCC3(C=Cc4ccccc43)CC2)ccc1COc1ccc(CCC(=O)O)c(F)c1] | 502 |
| 13 | 3-(2-Fluoro-4-{[3-fluoro-4-(1'H-spiro[indene-1,4'-piperidin]-1'-ylmethyl)benzyl]oxy}phenyl)propanoic acid | 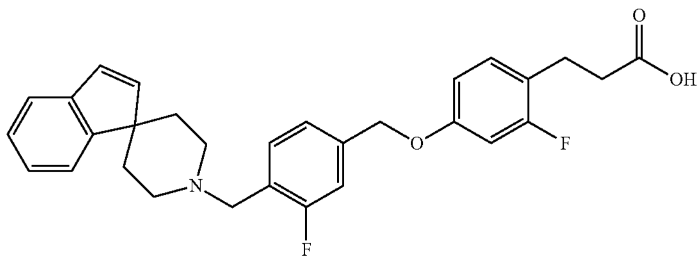 [SMILES: O=C(O)CCc1ccc(OCc2ccc(CN3CCC4(C=Cc5ccccc54)CC3)c(F)c2)cc1F] | 490 |
| 14 | (3S)-3-(4-{[3-Fluoro-4-(1'H-spiro[indene-1,4'-piperidin]-1'-ylmethyl)benzyl]oxy}phenyl)hex-4-ynoic acid | 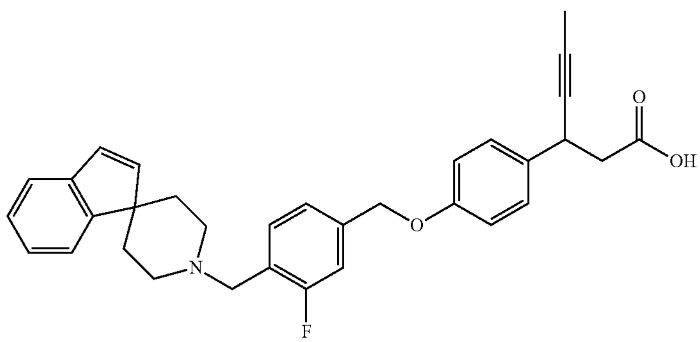 [SMILES: CC#CC(CC(=O)O)c1ccc(OCc2ccc(CN3CCC4(C=Cc5ccccc54)CC3)c(F)c2)cc1] | 510 |
| 15 | 3-(2-Fluoro-4-{[4-(1'H-spiro[indene-1,4'-piperidin]-1'-ylmethyl)-3-(trifluoromethyl)benzyl]oxy}phenyl)propanoic acid | 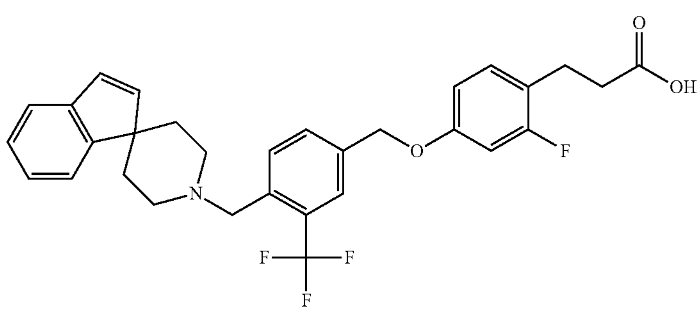 [SMILES: O=C(O)CCc1ccc(OCc2ccc(CN3CCC4(C=Cc5ccccc54)CC3)c(C(F)(F)F)c2)cc1F] | 540 |
| 16 | (3S)-3-(4-{[4-(2,3-Dihydro-1'H-spiro[indene-1,4'-piperidin]-1'-ylmethyl)-3-(trifluoromethyl)benzyl]oxy}phenyl)hex-4-ynoic acid | 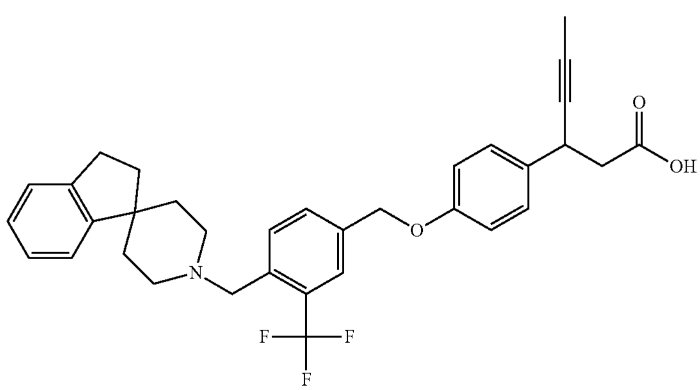 [SMILES: CC#CC(CC(=O)O)c1ccc(OCc2ccc(CN3CCC4(CCc5ccccc54)CC3)c(C(F)(F)F)c2)cc1] | 562 |

-continued

| Ex No. | Chemical Name | Structure | ESI/MS (m/z) (M + H) |
|---|---|---|---|
| 17 | 3-(4-{[4-(2,3-Dihydro-1'H-spiro[indene-1,4'-piperidin]-1'-ylmethyl)-3-(trifluoromethyl)benzyl]oxy}-2-fluorophenyl)propanoic acid | 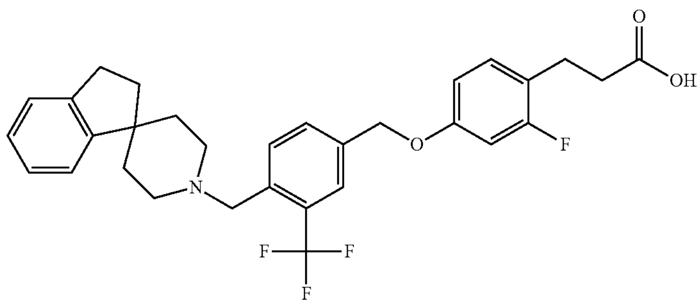 [SMILES: O=C(O)CCc1ccc(OCc2ccc(CN3CCC4(CCc5ccccc54)CC3)c(C(F)(F)F)c2)cc1F] | 542 |
| 18 | 3-(2-Fluoro-4-{[3-methoxy-4-(1'H-spiro[indene-1,4'-piperidin]-1'-ylmethyl)benzyl]oxy}phenyl)propanoic acid | 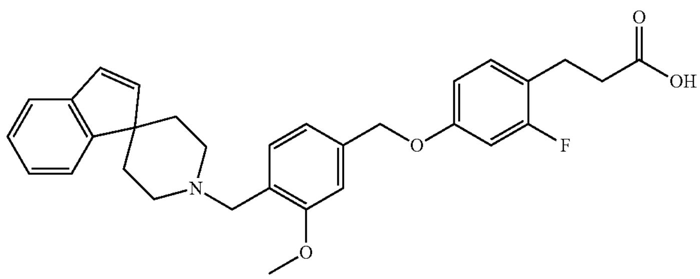 [SMILES: COc1cc(COc2ccc(CCC(=O)O)c(F)c2)ccc1CN1CCC2(C=Cc3ccccc32)CC1] | 502 |
| 19 | (3S)-3-(4-{[3-Methoxy-4-(1'H-spiro[indene-1,4'-piperidin]-1'-ylmethyl)benzyl]oxy}phenyl)hex-4-ynoic acid | 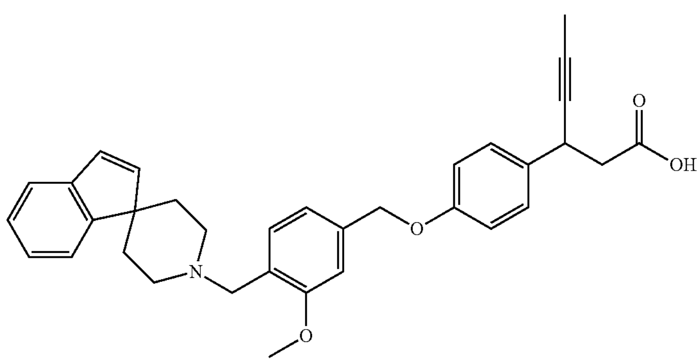 [SMILES: CC#CC(CC(=O)O)c1ccc(OCc2ccc(CN3CCC4(C=Cc5ccccc54)CC3)c(OC)c2)cc1] | 521 |
| 20 | 3-[2-Fluoro-4-({3-methoxy-4-[(1-methyl-1,2-dihydro-1'H-spiro[indole-3,4'-piperidin]-1'-yl)methyl]benzyl}oxy)phenyl]propanoic acid | 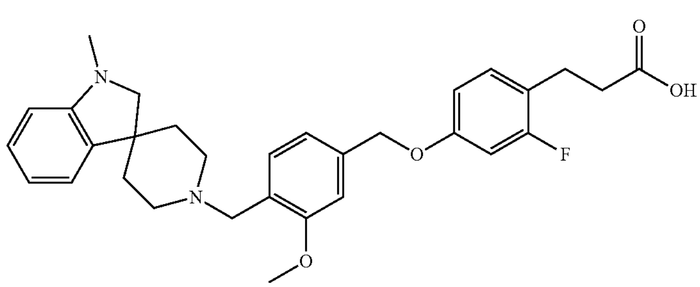 [SMILES: COc1cc(COc2ccc(CCC(=O)O)c(F)c2)ccc1CN1CCC2(CC1)CN(C)c1ccccc12] | 518 |

| Ex No. | Chemical Name | Structure | ESI/MS (m/z) (M + H) |
|---|---|---|---|
| 21 | (3S)-3-[4-({3-Methxoy-4-[(1-methyl-1,2-dihydro-1'H-spiro[indole-3,4'-piperidin]-1'-yl)methyl]benzyl}oxy)phenyl]hex-4-ynoic acid | 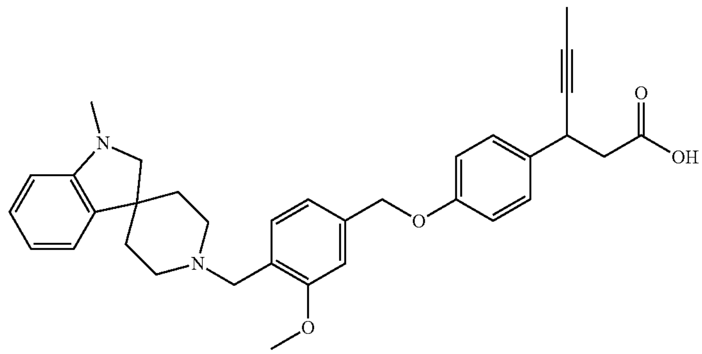 [SMILES: CC#CC(CC(=O)O)c1ccc(OCc2ccc(CN3CCC4(CC3)CN(C)c3ccccc34)c(OC)c2)cc1] | 538 |
| 22 | 3-(2-Fluoro-4-{[3-methyl-4-(1'H-spiro[indene-1,4'-piperidin]-1'-ylmethyl)benzyl]oxy}phenyl)propanoic acid | 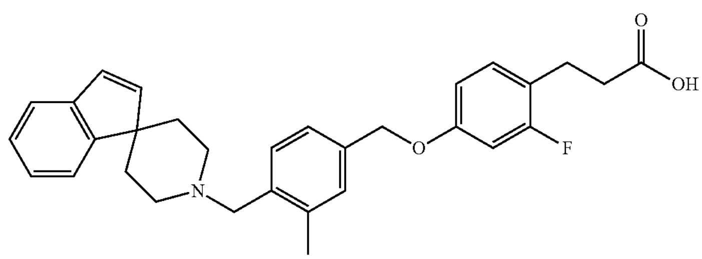 [SMILES: Cc1cc(COc2ccc(CCC(=O)O)c(F)c2)ccc1CN1CCC2(C=Cc3ccccc32)CC1] | 486 |
| 23 | (3S)-3-(4-{[3-Methyl-4-(1'H-spiro[indene-1,4'-piperidin]-1'-ylmethyl)benzyl]oxy}phenyl)hex-4-ynoic acid | 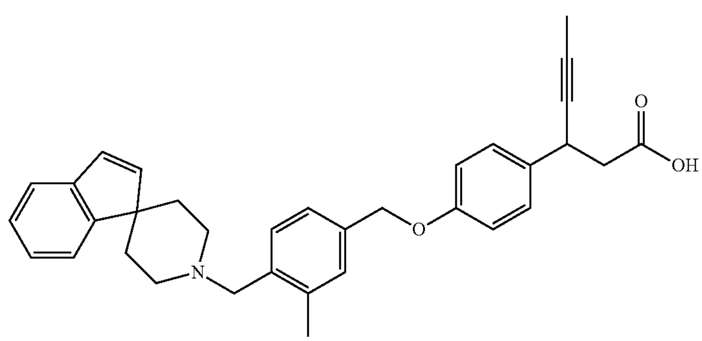 [SMILES: CC#CC(CC(=O)O)c1ccc(OCc2ccc(CN3CCC4(C=Cc5ccccc54)CC3)c(C)c2)cc1] | 506 |

Example 24

(3S)-3-[4-({4-[(1-Methyl-1,2-dihydro-1'H-spiro[indole-3,4'-piperidin]-1'-yl)methyl]benzyl}oxy)phenyl]hex-4-ynoic acid

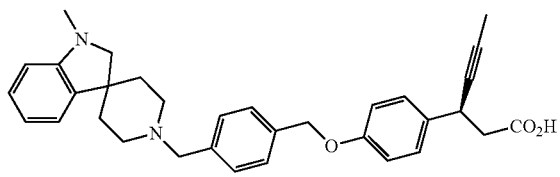 [SMILES: CC#C[C@@H](CC(=O)O)c1ccc(OCc2ccc(CN3CCC4(CC3)CN(C)c3ccccc34)cc2)cc1]

To a solution of ethyl (3S)-3-[4-[[4-[(1-methylspiro[indoline-3,4'-piperidine]-1'-yl)methyl]phenyl]methoxy]phenyl]hex-4-ynoate (0.09 g, 0.167 mmol) in ethanol:water (3:1, 2 mL) is added KOH (0.047 g, 0.838 mmol) and stirred at room temperature for 2 hours. The reaction mixture is evaporated to dryness. The residue is re-dissolved in water (5 mL) and washed with $Et_2O$ (3×5 mL). The aqueous layer is acidified with 1.5 N HCl to pH ~6. The solid precipitate is filtered, washed with water, and dried. The solid is dissolved in dichloromethane (40 mL) washed with 10% $NaHCO_3$ (15 mL), water, (15 mL) and saturated ammonium chloride solution (15 mL), dried, filtered, and evaporated to dryness to give the title compound as an off-white solid (0.05 g, 58.2%). ESI/MS m/z 509 (M+H)⁺.

The following compounds are prepared essentially as described by the method of Example 24.

| Ex No. | Chemical Name | Structure | ESI/MS (m/z) (M + H) |
|---|---|---|---|
| 25 | 3-[2-Fluoro-4-({4-[(1-methyl-1,2-dihydro-1'H-spiro[indole-3,4'-piperidin]-1'-yl)methyl]benzyl}oxy)phenyl]propanoic acid | 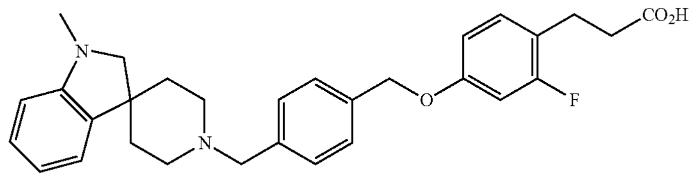 [SMILES: CN1CC2(CCN(Cc3ccc(COc4ccc(CCC(=O)O)c(F)c4)cc3)CC2)c2ccccc21] | 489 |
| 26 | 3-[4-({4-[(7-Chloro-1-methyl-1,2-dihydro-1'H-spiro[indole-3,4'-piperidin]-1'-yl)methyl]benzyl}oxy)-2-fluorophenyl]propanoic acid | 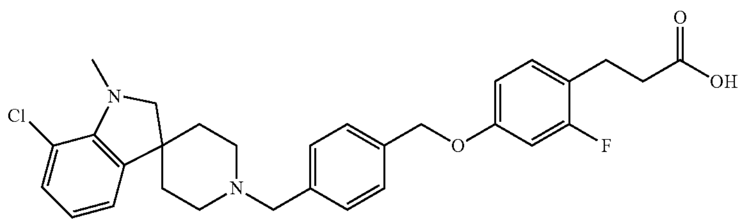 [SMILES: CN1CC2(CCN(Cc3ccc(COc4ccc(CCC(=O)O)c(F)c4)cc3)CC2)c2cccc(Cl)c21] | 523 |
| 27 | (3S)-3-[4-({4-[(7-Chloro-1-methyl-1,2-dihydro-1'H-spiro[indole-3,4'-piperidin]-1'-yl)methyl]benzyl}oxy)phenyl]hex-4-ynoic acid | 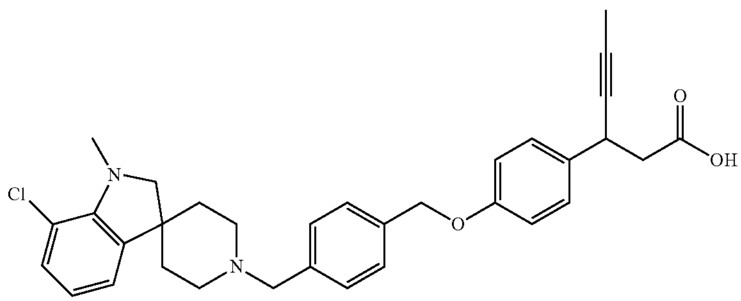 [SMILES: CC#CC(CC(=O)O)c1ccc(OCc2ccc(CN3CCC4(CC3)CN(C)c3c(Cl)cccc34)cc2)cc1] | 543 |
| 28 | 3-[2-Fluoro-4-({4-[(5-fluoro-1-methyl-1,2-dihydro-1'H-spiro[indole-3,4'-piperidin]-1'-yl)methyl]benzyl}oxy)phenyl]propanoic acid | 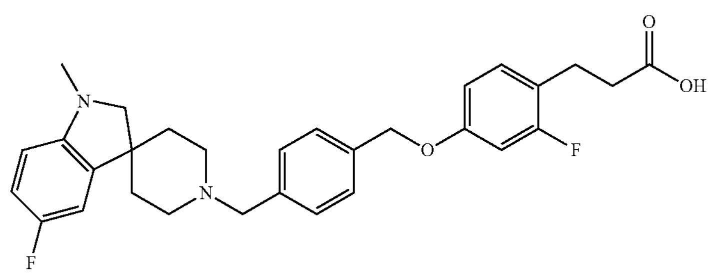 [SMILES: CN1CC2(CCN(Cc3ccc(COc4ccc(CCC(=O)O)c(F)c4)cc3)CC2)c2cc(F)ccc21] | 507 |
| 29 | 3-[2-Fluoro-4-({4-[(5-methoxy-1-methyl-1,2-dihydro-1'H-spiro[indole-3,4'-piperidin]-1'-yl)methyl]benzyl}oxy)phenyl]propanoic acid | 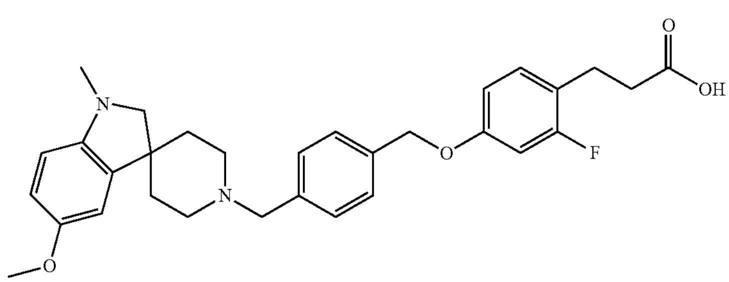 [SMILES: COc1ccc2c(c1)C1(CCN(Cc3ccc(COc4ccc(CCC(=O)O)c(F)c4)cc3)CC1)CN2C] | 519 |

| Ex No. | Chemical Name | Structure | ESI/MS (m/z) (M + H) |
|---|---|---|---|
| 30 | (3S)-3-[4-({4-[(5-Methoxy-1-methyl-1,2-dihydro-1'H-spiro[indole-3,4'-piperidin]-1'-yl)methyl]benzyl}oxy)phenyl]hex-4-ynoic acid | 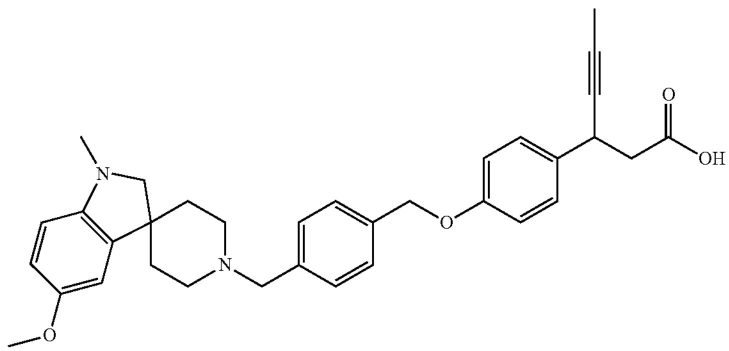 [SMILES: CC#CC(CC(=O)O)c1ccc(OCc2ccc(CN3CCC4(CC3)CN(C)c3ccc(OC)cc34)cc2)cc1] | 539 |
| 31 | (3S)-3-[4-({4-[(1,5-Dimethyl-1,2-dihydro-1'H-spiro[indole-3,4'-piperidin]-1'-yl)methyl]benzyl}oxy)phenyl]hex-4-ynoic acid | 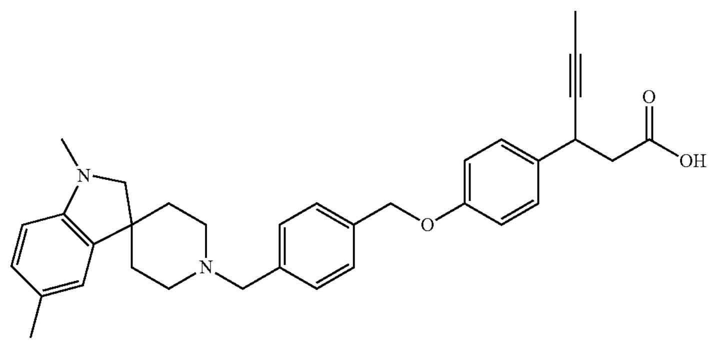 [SMILES: CC#CC(CC(=O)O)c1ccc(OCc2ccc(CN3CCC4(CC3)CN(C)c3ccc(C)cc34)cc2)cc1] | 523 |
| 32 | 3-{2-Fluoro-4-[(4-{[1-methyl-5-(trifluoromethyl)-1,2-dihydro-1'H-spiro[indole-3,4'-piperidin]-1'-yl]methyl}benzyl)oxy]phenyl}propanoic acid | 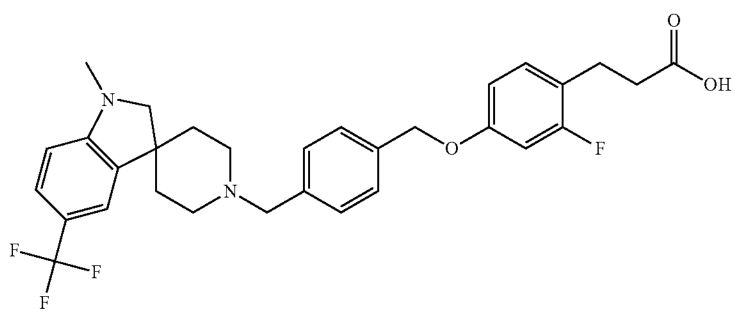 [SMILES: CN1CC2(CCN(Cc3ccc(COc4ccc(CCC(=O)O)c(F)c4)cc3)CC2)c2cc(C(F)(F)F)ccc21] | 557 |
| 33 | (3S)-3-{4-[(4-{[1-Methyl-5-(trifluoromethyl)-1,2-dihydro-1'H-spiro[indole-3,4'-piperidin]-1'-yl]methyl}benzyl)oxy]phenyl}hex-4-ynoic acid | 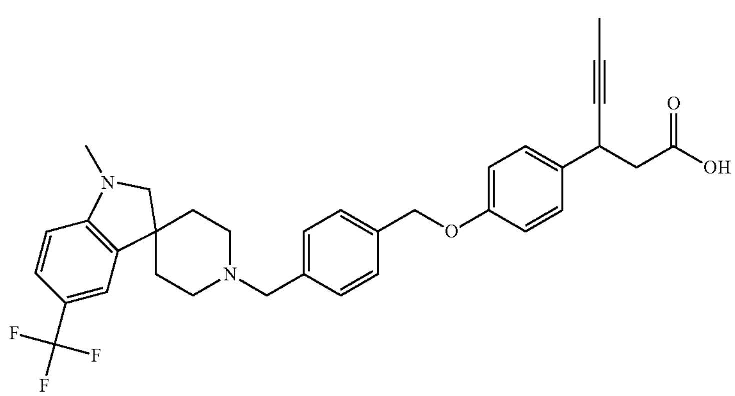 [SMILES: CC#CC(CC(=O)O)c1ccc(OCc2ccc(CN3CCC4(CC3)CN(C)c3ccc(C(F)(F)F)cc34)cc2)cc1] | 577 |

| Ex No. | Chemical Name | Structure | ESI/MS (m/z) (M + H) |
|---|---|---|---|
| 34 | (3S)-3-[4-({4-[(1-Phenyl-1,2-dihydro-1'H-spiro[indole-3,4'-piperidin]-1'-yl)methyl]benzyl}oxy)phenyl]hex-4-ynoic acid | 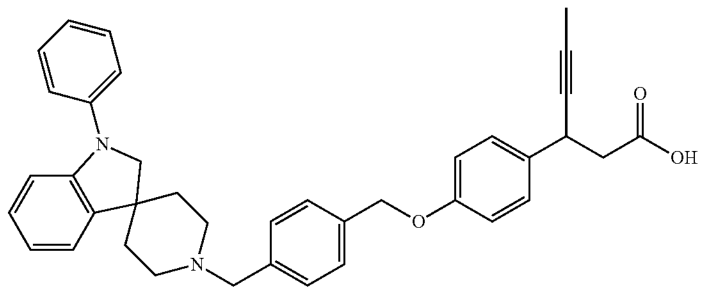 [SMILES: CC#CC(CC(=O)O)c1ccc(OCc2ccc(CN3CCC4(CC3)CN(c3ccccc3)c3ccccc34)cc2)cc1] | 571 |
| 35 | 3-[2-Fluoro-4-({4-[(3-oxo-2,3-dihydro-1'H-spiro[indene-1,4'-piperidin]-1'-yl)methyl]benzyl}oxy)phenyl]propanoic acid | 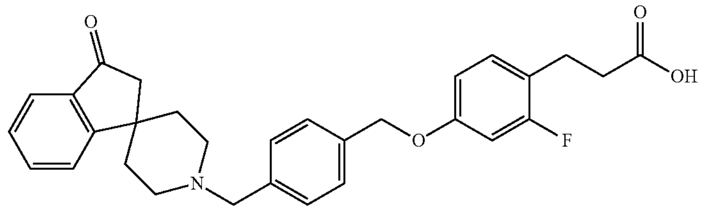 [SMILES: O=C(O)CCc1ccc(OCc2ccc(CN3CCC4(CC3)CC(=O)c3ccccc34)cc2)cc1F] | 488 |
| 36 | 3-(4-{[4-(1,2-Dihydro-1'H-spiro[indole-3,4'-piperidin]-1'-ylmethyl)benzyl]oxy}-2-fluorophenyl)propanoic acid | 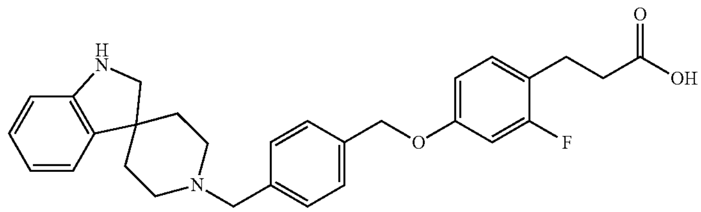 [SMILES: O=C(O)CCc1ccc(OCc2ccc(CN3CCC4(CC3)CNc3ccccc34)cc2)cc1F] | 475 |
| 37 | (3S)-3-[4-[[4-(Spiro[indane-1,4'-piperidine]-1'-ylmethyl)phenyl]methoxy]phenyl]hex-4-ynoic acid | 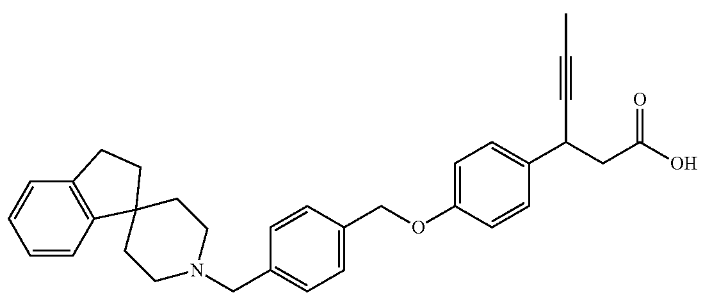 [SMILES: CC#CC(CC(=O)O)c1ccc(OCc2ccc(CN3CCC4(CCc5ccccc54)CC3)cc2)cc1] | 494 |

Example 38

3-(4-{[4-(2,3-Dihydro-1'H-spiro[indene-1,4'-piperidin]-1'-ylmethyl)benzyl]oxy}-2-fluorophenyl)propanoic acid

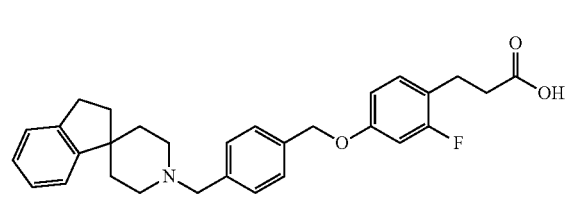 [SMILES: O=C(O)CCc1ccc(OCc2ccc(CN3CCC4(CCc5ccccc54)CC3)cc2)cc1F]

To a stirred solution of ethyl 3-[2-fluoro-4-[[4-(spiro[indane-1,4'-piperidine]-1'-ylmethyl)phenyl]methoxy]phenyl]propanoate (0.22 g, 0.43 mmol) in MeOH (15 mL) is added LiOH.H₂O (0.20 g, 4.8 mmol) and the mixture is heated at 85° C. for 45 min in a microwave oven. Methanol is evaporated and the residue is dissolved in water. The pH is adjusted to approximately 6 and a solid precipitate is filtered, collected, and dried to give the title compound as an off-white solid (0.12 g, 55.0%). ESI/MS 474.6 (M+H)⁺.

Example 39

3-[4-({4-[(1,5-Dimethyl-1,2-dihydro-1'H-spiro[indole-3,4'-piperidin]-1'-yl)methyl]benzyl}oxy)-2-fluorophenyl]propanoic acid

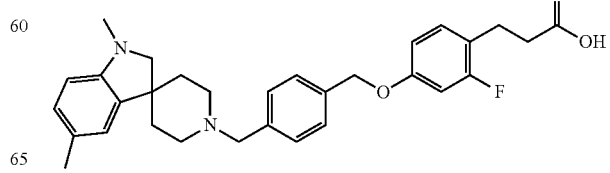

To a stirring solution of 1,5-dimethylspiro[indoline-3,4′-piperidine] (0.30 g, 1.38 mmol), and ethyl 3-(4-{[4-(bromomethyl)benzyl]oxy}-2-fluorophenyl) propanoate (0.60 g, 1.52 mmol), in DMF (10 mL), is added $Cs_2CO_3$ (0.89 g, 2.76 mmol). The reaction mixture is stirred at room temperature for 12 hours, diluted with water (100 mL), and extracted with $Et_2O$. The organic layer is separated, dried over $Na_2SO_4$, and concentrated under vacuum to give (0.2 g, 0.376 mmol). The material is dissolved in ethanol/water (4 mL/1 mL) and KOH (0.063 g, 1.12 mmol) is added. The mixture is stirred at room temperature for 4 h and ethanol is evaporated. The pH is adjusted to approximately 5 with 1 N HCl solution and the precipitate formed is filtered to give the title compound as an off-white solid (0.13 g, 18.6%). ESI/MS m/z 503 $(M+H)^+$.

The causes of T2D are believed to be two-fold, insulin resistance, and progressive failure of pancreatic beta cells to produce adequate amounts of insulin to lower circulating glucose levels. Insulin resistance develops when normal insulin levels are unable to dispose of circulating plasma glucose into target tissues, including skeletal muscle and adipose tissue. As the pancreas produces more insulin to compensate for the excessively high glucose levels due to insulin resistance, the pancreatic beta cells eventually become exhausted and no additional insulin is available for secretion. Over time, the pancreatic beta cells completely fail and a person with T2D becomes similar to one with type 1 diabetes. High levels of circulating glucose is the hallmark of diabetes and can eventually lead to serious complications such as heart disease and strokes, high blood pressure, blindness, kidney and nerve damage, infections, and gum disease. Therefore, it is important to control and treat T2D as early as possible with exercise; a proper diet; oral anti-diabetic therapies; and eventually with insulin. Compounds claimed by the present invention provide additional pharmacological treatment options. Compounds selectively modulating GPR40 may be particularly desirable.

GPR40: Information

Results of studies using transgenic mice over-expressing the human GPR40 gene under control of the insulin II promoter recently reported by Nagasumi further support that GPR40 plays an important role in the regulation of GDIS and plasma glucose levels in-vivo, especially in rodent models of insulin resistance. Nagasumi K, et. al., *Overexpression of GPR40 in pancreatic β-cells augments glucose-stimulated insulin secretion and improves glucose tolerance in normal and diabetic mice* Diabetes 58: 1067-1076, 2009. These findings further support that the development of new GPR40 modulator compounds may be particularly desired for use in the treatment of T2D.

Calcium Flux Primary Assay

The compounds exemplified herein are tested essentially as described below and exhibit an $EC_{50}$ value for the Calcium Flux Primary assay of lower than 1 µM.

This assay is used to screen compounds by measuring the increase in intracellular calcium levels that results when a ligand binds and activates GPR40, thus demonstrating the potency and efficacy of GPR40 agonists. HEK293 cells over expressing the human GPR40 cDNA maintained in Dulbecco's modified Eagle's medium with F12 medium in 3:1 ratio supplemented with 10% FBS and 800 µg/ml geneticin at 37° C. and 5% $CO_2$ are employed for the study. Agonist assays are performed using a Calcium 4 Dye assay kit (Molecular Devices) in the presence (0.1%) or absence of fatty acid free BSA in the assay buffer (1×HBSS (Hank's Balanced Salt Solution) & 20 mM HEPES (4-(2-hydroxyethyl)-1-piperazineethanesulfonic acid). Receptor activation is measured as an increase in intracellular calcium using the Fluorometric Imaging Plate Reader (FLIPR). Maximum change in fluorescence over the base line is used to determine agonist response. $EC_{50}$ (effective concentration at half the maximal response) value of the compound is calculated using Excel Fit software (version 4; IDBS) by plotting concentration vs relative fluorescence units (RFUs). Percent efficacy is calculated based on the maximal response exhibited by compound compared to the natural ligand, linoleic acid. The test compound of Example 1 has an $EC_{50}$ of 186+/−93 nM with 91+/−10% efficacy when examined in this assay. These results further demonstrate the desired potency and efficacy as GPR-40 agonists.

Glucose Dependent Insulin Secretion (GDIS) Assays

Because activation of GPR40 is known to result in insulin secretion which is dependent on high glucose concentrations, two separate assay systems (insulinoma cell line and primary rodent islets) are developed to further characterize compounds that are known to increase intracellular calcium in the GPR40 primary assay discussed above.

GDIS assays are performed using the mouse insulinoma cell line Min6. Min6 cells are maintained in Dulbecco's Modified Eagle's Medium (DMEM) containing non-essential amino acids, 10% FBS, 50 mM 2-mercaptoethanol and 1% penicillin and streptomycin at 37° C. plus 5% $CO_2$. On the day of the experiment, the cells are washed twice with 200 µl of pre-warmed Krebs-ringer buffer without glucose. Addition of 200 µL of pre-warmed Krebs-ringer buffer containing 2.5 mM glucose is used to starve the cells followed by the addition of compounds in the presence of a high concentration of glucose (25 mM). The plate is incubated at 37° C. for 2 hours. At the end of the 2 h incubation, the supernatant is gently transferred into a Millipore filter plate and spun at 200 g (gravitational force) for 3 minutes. Insulin is assayed using a Mercodia Insulin estimation kit. Addition of Example 1 at 1 µM plus 25 mM glucose to the Min6 cells resulted in a statistically significant, two-fold increase in insulin secretion compared to that achieved with 25 mM glucose alone.

GDIS assays using primary rodent pancreatic islets of Langerhans are also used to characterize exemplified compounds. Pancreatic islets are isolated from male SD (Sprague Dawley) rats by collagenase digestion and Histopaque density gradient separation. The islets are cultured overnight in RPMI-1640 medium with GlutaMAXn (stabilized, dipeptide form of L-glutamine (Invitrogen catalog #61870-010)) to facilitate recovery from the isolation process. Insulin secretion is determined by a 90 minute incubation in EBSS (Earle's Balances Salt Solution) buffer in a 48-well plate. Briefly, islets are first preincubated in EBSS with 2.8 mM glucose for 30 min and are then transferred to a 48-well plate (four islets/well) containing 150 µl 2.8 mM glucose and incubated with 150 µl of EBSS with 2.8 or 11.2 mM glucose in the presence or absence of test compounds for 90 minutes. The buffer is removed from the wells at the end of the incubation and assayed for insulin levels using the Rat Insulin ELISA kit (Mercodia). In this assay system, administration of Example 1 at different concentrations results in a 2- to 4-fold increase in insulin compared to that achieved with 11.2 mM glucose alone.

Selectivity Assays:

Peroxisome Proliferator-Activated Receptor (PPAR) α, δ, and γ Binding and Functional Assays:

Because GPR40 is known to be activated by ligands to PPARγ exemplified compounds are examined in PPARα, PPARδ, and PPARγ binding and functional assays to determine the selectivity of exemplified compounds for GPR40. Compounds exemplified herein are tested essentially as described below for PPAR binding and generally have binding values greater than 1000 nM with 10 µM concentrations of test compound and are thus considered negative for PPAR activity.

Binding affinities of compounds for the PPAR α, δ, and γ receptors are assessed using Scintillation Proximity Assay (SPA) technology. Biotinylated oligonucleotide Direct Repeat 2 (DR2) is used for binding the receptors to Yttrium silicate streptavidin-coated SPA beads. PPAR α, δ, γ and retinoid X receptor (RXR) α are over expressed in HEK293 cells, and cell lysates containing the specific receptors are used in the individual assays. The DR2 is attached to the SPA beads over a 30 minute period in a binding buffer containing 10 mM HEPES pH 7.8, 80 mM KCl, 0.5 mM MgCl$_2$, 1 mM DTT, 0.5% 3[(3-cholamidopropyl)dimethylammonio]-propanesulfonic acid (CHAPS), and 4.4% bovine serum. The cell lysates are incubated in each well with one of 11 concentrations of compound in the presence of a radio-labeled (~0.033.8 μCi$^3$H) PPAR α/δ dual agonist reference compound for the alpha and delta receptor assays and a radio-labeled (~0.037.3 μCi $^3$H) PPARγ agonist reference compound for the gamma receptor assays, 110.3 μg of Yttrium SPA Streptavidin coated beads, 0.126 nM HD Oligo DR2, and either 0.3 μg PPARα with 0.5 μg RXRα, 0.5 μg PPARδ with 0.5 μg RXRα, or 1.25 μg PPARγ with 3.03 μg RXRα in the binding buffer above plus 14% glycerol and 5 μg of sheared salmon sperm DNA. Non-specific binding is determined in the presence of 10,000 nM of the unlabeled PPAR α/δ dual agonist reference compound for the alpha and delta receptor assays and the PPARγ agonist reference compound for the gamma receptor assay. The binding reaction (100 μl per well in a 96 well [Costar 3632] plate) is incubated for 10 h and counted disintegration per minutes (dpm) on a Wallac Microbeta. Receptor binding affinity (IC$_{50}$) for the compounds is determined by fitting an 11 point concentration-response curve with a 4-parameter logistic equation. K$_i$, is determined from the IC$_{50}$ using the Cheng-Prussoff equation and Kd determined by saturation binding. For the compound of Example 1, no binding is detected in any of the three PPAR binding assays with concentrations up to 10 μM. Thus, the assays set forth herein support that the compound of Example 1 selectively activates GPR-40 while avoiding the undesired PPAR activity. Exemplified compounds relative IC50s are generally greater than 10 uM for the PPAR isoforms, supporting that the compounds avoid PPAR activity while providing the desired GPR-40 activation.

Gal4 PPARα, Gal4 PPARδ, and PPARγ reporter functional assays are also used to monitor the selectivity of exemplified compounds. CV1 cells, which are derived from the renal tissue of an African green monkey, are transfected with various receptor and reporter plasmids using Fugene. For the Gal4 PPARα and PPARδ assays, a reporter plasmid containing five tandem copies of the yeast transcription protein Gal4 response element, cloned upstream of a firefly luciferase gene driven by the major late promoter of adenovirus, is transfected together with a Simian Virus 40 (SV40) driven plasmid constitutively expressing a hybrid protein containing the Gal4 DNA binding domain (DBD), and either the PPARα or PPARδ ligand binding. For the PPARγ assay, plasmids encoding PPARγ and RXRα, both driven by a cytomegalovirus (CMV) promoter are transfected together with a plasmid containing luciferase reporter cDNA driven by the TK promoter and a receptor response element (2×PPRE). Cells are transfected in T225 cm$^2$ cell culture flasks in DMEM media with 5% charcoal-stripped FBS. After an overnight incubation, transfected cells are trypsinized, plated in opaque 96 well dishes (15,000 cells/well) in DMEM media containing 5% charcoal-stripped FBS, incubated for 4 h, and exposed to 0.17 ηM to 10 μM of test compounds or reference compound in half log dilutions. After 24 hours incubation with compounds, cells are lysed and luciferase activity is determined as a measure of receptor activation by luminescence. Data are fitted to a four parameter-fit logistics model to determine EC$_{50}$ values. The maximum percent stimulation is determined versus maximum stimulation obtained with 10 μM of an appropriate PPAR agonist reference compound. No functional activation of PPARα, PPARδ, or PPARγ is detected with the compound of Example 1 when examined up to 10 μM in the specific PPAR co-transfection (CTF)/functional assays described above. Thus, the assay supports that the exemplified compounds avoid PPAR agonist activity, as desired.

In Vivo Efficacy: Intraperitoneal Glucose Tolerance Test (IP-GTT)

To examine the ability of exemplified compounds to activate GPR40 in-vivo resulting in anti-diabetic efficacy, i.e. an increase in insulin and reduction in glucose levels, a 4-day intraperitoneal glucose tolerance test (ipGTT) study is completed with each compound.

Male Balb/c (Albino mice) mice (8-9 weeks of age) are single housed and fed with normal rodent chow diet and water ad libitum. Animals are weighed and randomized by body weight and daily body weights are recorded. Upon study initiation, animals are dosed once per day orally for three days using a formulation carrying methylcellulose and tween-80. On the night before the 4-day IPGTT study, animals are fasted overnight in clean cages. On the morning of the IPGTT (Day 4), animals are dosed orally with compound or vehicle alone 60 minutes prior to the IPGTT (glucose 2 g/kg, i.p.). Blood glucose levels are determined from tail bleeds taken at 0, 3, 7, 15, 30, and 60 min after glucose challenge. Plasma is isolated and used to estimate respective insulin levels. The blood glucose excursion profile from t=0 to t=60 min is used to integrate an area under the curve (AUC) for each treatment. Percent lowering in glucose is calculated from the AUC data of the compounds with respect to the AUC of vehicle group. The test compound is orally administered at 0.03, 0.1, 0.3, 1.0, or 3.0 mg/kg, and a positive control is administered at 10 mg/kg. No concentration of the compound of Example 1 or the positive control significantly lowered glucose levels at the 3 minute time point during the GTT. In contrast, glucose levels are significantly lowered with the 0.3, 1.0, and 3.0 mg/kg doses of the compound of Example 1 and the positive control at the 7 minute time point and with 0.1, 0.3, 1.0, and 3.0 mg/kg doses of the compound of Example 1 and with the positive control at the 15 minute time point. All doses of the compound of Example 1 and the positive control significantly lowered glucose levels at the 30 and 60 minute time points. The ED$_{50}$ for the compound of Example 1 based on AUCs for glucose lowering is 0.09 mg/kg. In this study, insulin levels were significantly elevated at the 1.0 and 3.0 mg/kg dose of the compound of Example 1 at the 3 minute time point which is consistent with activation of GPR40. The results of this assay support the compound's activation of GPR-40, with resulting in vivo anti-diabetic efficacy.

We claim:
1. A compound of the formula:

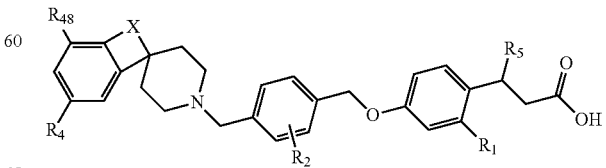

or a pharmaceutically acceptable salt thereof;

wherein:
R$_1$ is selected from the group consisting of H, F and Cl;
R$_2$ is selected from the group consisting of H, C$_{1-3}$alkyl, CF$_3$, OCH$_3$, F, and Cl;
R$_4$ and R$_4$a are each independently selected from the group consisting of H, OCH$_3$, C$_{1-3}$alkyl, CF$_3$, and F, wherein at least one selected from the group consisting of R$_4$ and R$_4$a is H;
R$_5$ is H or C≡CCH$_3$;
X is selected from the group consisting of —CH(R$_3$)CH$_2$—, —C(R$_3$)═CH—, —N(R$_7$)CH$_2$—. and —C(O)CH$_2$—;
R$_3$ is selected from the group consisting of H and C$_{1-3}$alkyl; and
R$_2$ is selected from the group consisting of H, C$_{1-3}$alkyl, and phenyl.

2. A compound or salt thereof as claimed by claim 1 wherein X is selected from the group consisting of —N(R$_7$)CH$_2$—, —C(R$_3$)═CH—, and —CH(R$_3$)CH$_2$.

3. A compound or salt thereof as claimed by claim 2 wherein X is —C(R$_3$)═CH—.

4. A compound or salt thereof as claimed by claim 3 wherein R$_3$ is selected from the group consisting of H and CH$_3$.

5. A compound or salt thereof as claimed by claim 4 wherein R$_3$ is H.

6. A compound or salt thereof as claimed by claim 2 wherein X is —N(R$_7$)CH$_2$—.

7. A compound or salt thereof as claimed by claim 6 wherein R$_2$ is selected from the group consisting of H, C$_{1-3}$alkyl.

8. A compound or salt thereof as claimed by claim 7 wherein R$_2$ is CH$_3$.

9. A compound or salt thereof as claimed by claim 1 wherein R$_4$ is selected from the group consisting of OCH$_3$, CH$_3$, CF$_3$, and F.

10. A compound or salt thereof as claimed by claim 1 wherein R$_{4a}$ is selected from the group consisting of H and Cl.

11. A compound or salt thereof as claimed by claim 8 wherein R$_4$ and R$_{4a}$ are each H.

12. A compound or salt thereof as claimed by claim 1 wherein R$_2$ is selected from the group consisting of H, OCH$_3$, CH$_3$ and CF$_3$.

13. A compound or salt thereof as claimed by claim 12 wherein R$_2$ is H.

14. A compound or salt thereof as claimed by claim 1 wherein R$_5$ is C≡CCH$_3$.

15. A compound or salt thereof as claimed by claim 1 wherein R$_1$ is selected from the group consisting of F and Cl; and R$_5$ is H.

16. A compound or salt thereof as claimed by claim 14 wherein R$_1$ is H.

17. A compound or salt thereof as claimed by claim 1 wherein the compound is the S isomer.

18. A compound as claimed by claim 17 wherein the compound is a pharmaceutically acceptable salt.

19. A pharmaceutical composition comprising a pharmaceutically acceptable carrier and at least one compound as claimed by claim 1 or a pharmaceutically acceptable salt thereof.

20. A method for treating type 2 diabetes in a mammal, comprising the step of administering to the mammal a compound as claimed by claim 1 or a pharmaceutically acceptable salt thereof.

21. A compound of the formula

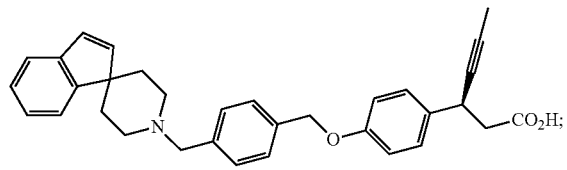 [SMILES: CC#C[C@@H](CC(=O)O)c1ccc(OCc2ccc(CN3CCC4(C=Cc5ccccc54)CC3)cc2)cc1]

or a pharmaceutically acceptable salt thereof.

22. A compound of the formula

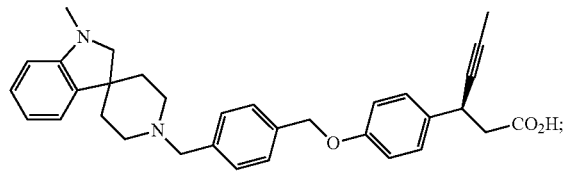

or a pharmaceutically acceptable salt thereof.

23. An intermediate compound of the formula:

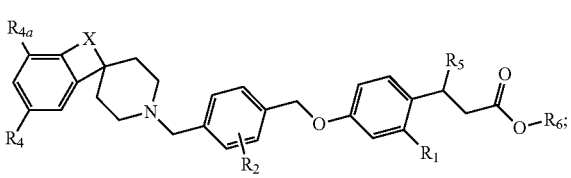

or a salt thereof;
wherein:
R$_1$ is selected from the group consisting of H, F and Cl;
R$_2$ is selected from the group consisting of H, C$_{1-3}$alkyl, CF$_3$, OCH$_3$, F, and Cl;
R$_4$ and R$_4$a are each independently selected from the group consisting of H, OCH$_3$, C$_{1-3}$alkyl, CF$_3$, and F, wherein at least one selected from the group consisting of R$_4$ and R$_4$a is H;
R$_5$ is H or C≡CCH$_3$;
R$_6$ is selected from the group consisting of C$_{1-3}$ alkyl;
X is selected from the group consisting of —CH(R$_3$)CH$_2$—, —C(R$_3$)═CH—, —N(R$_7$)CH$_2$—. and —C(O)CH$_2$—;
R$_3$ is selected from the group consisting of H and C$_{1-3}$alkyl; and
R$_2$ is selected from the group consisting of H, C$_{1-3}$alkyl, C(O)OC$_{1-4}$alkyl, and phenyl.

24. A compound or salt thereof as claimed by claim 23 wherein R$_5$ is C≡CCH$_3$.

25. A compound or salt thereof as claimed by claim 23 wherein R$_1$ is selected from the group consisting of F and Cl; and R$_5$ is H.

* * * * *

UNITED STATES PATENT AND TRADEMARK OFFICE
CERTIFICATE OF CORRECTION

PATENT NO. : 8,383,642 B2  
APPLICATION NO. : 12/901597  
DATED : February 26, 2013  
INVENTOR(S) : Chafiq Hamdouchi et al.

Page 1 of 2

It is certified that error appears in the above-identified patent and that said Letters Patent is hereby corrected as shown below:

Title page, Column 1, item (73), (Assignee), line 1, please delete "Indidnapolis," and insert --Indianapolis,--, therefor.

Title page, Column 2, item (56), (Other Publications), line 1, please delete "Mellisa" and insert --Melissa--, therefor.

Title page, Column 2, item (57), (Abstract), line 2, please delete

"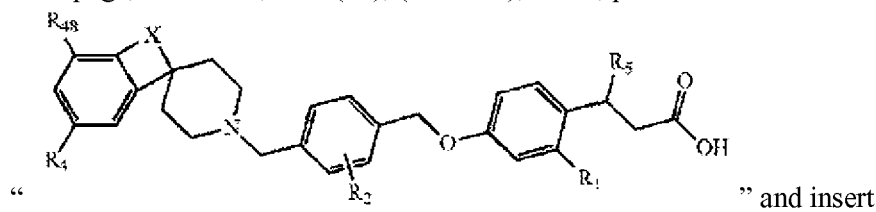" and insert

--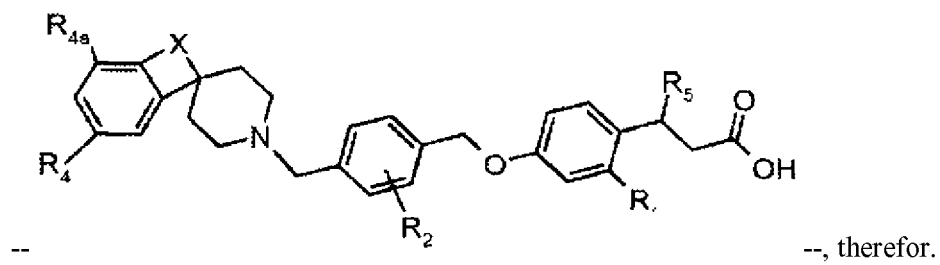--, therefor.

In the Specifications:

In Column 1, line 3, please delete "60/251,839" and insert --61/251,839--, therefor.

In Column 1, line 3, please delete "60/303,334," and insert --61/303,334,--, therefor.

In Column 1, line 4, please delete "22 Feb. 2010," and insert --11 Feb. 2010,--, therefor.

Signed and Sealed this  
Thirtieth Day of April, 2013

Teresa Stanek Rea  
*Acting Director of the United States Patent and Trademark Office*

CERTIFICATE OF CORRECTION (continued)
U.S. Pat. No. 8,383,642 B2

In the Claims:

In Column 56, Claim 1, lines 60-64, please delete

" 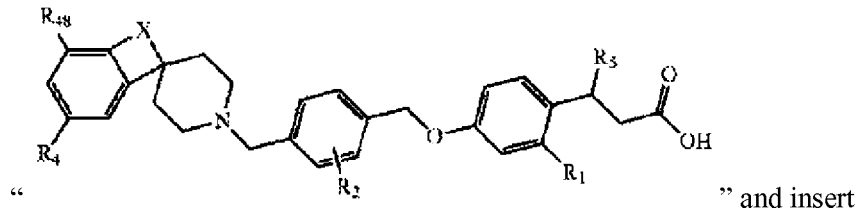 " and insert

-- 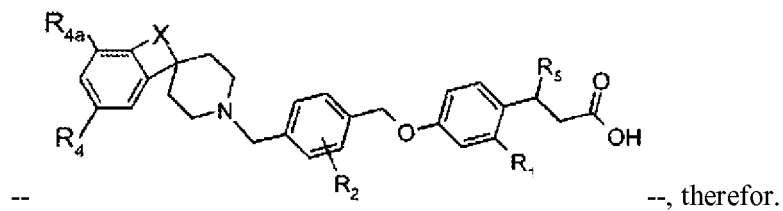 --, therefor.

In Column 57, Claim 1, line 5, please delete "R$_4$a" and insert --R$_{4a}$--, therefor.

In Column 57, Claim 1, line 8, please delete "R$_4$a" and insert --R$_{4a}$--, therefor.

In Column 57, Claim 1, line 12, please delete "—N(R$_7$)CH$_2$—." and insert --"—N(R$_7$)CH$_2$—,--, therefor.

In Column 57, Claim 1, line 16, please delete "R$_2$" and insert --R$_7$--, therefor.

In Column 57, Claim 7, line 31, please delete "R$_2$" and insert --R$_7$--, therefor.

In Column 57, Claim 8, line 34, please delete "R$_2$" and insert --R$_7$--, therefor.

In Column 58, Claim 23, line 44, please delete "R$_4$a" and insert --R$_{4a}$--, therefor.

In Column 58, Claim 23, line 47, please delete "R$_4$a" and insert --R$_{4a}$--, therefor.

In Column 58, Claim 23, line 50, please delete "—N(R$_7$)CH$_2$—." and insert --"–N(R$_7$)CH$_2$–,--, therefor.

In Column 58, Claim 23, line 54, please delete "R$_2$" and insert --R$_7$--, therefor.